(12) United States Patent
Caroli et al.

(10) Patent No.: US 12,427,226 B2
(45) Date of Patent: Sep. 30, 2025

(54) INTRAOCULAR LENS COMPOSITIONS

(71) Applicant: Teleon Holding B.V., Spankeren (NL)

(72) Inventors: Giuseppe Caroli, Deventer (NL); Ben Wanders, Angerlo (NL)

(73) Assignee: Teleon Holding B.V., Spankeren (NL)

( * ) Notice: Subject to any disclaimer, the term of this patent is extended or adjusted under 35 U.S.C. 154(b) by 584 days.

(21) Appl. No.: 17/430,005

(22) PCT Filed: Mar. 6, 2020

(86) PCT No.: PCT/NL2020/050146
§ 371 (c)(1),
(2) Date: Aug. 11, 2021

(87) PCT Pub. No.: WO2020/180185
PCT Pub. Date: Sep. 10, 2020

(65) Prior Publication Data
US 2022/0143267 A1  May 12, 2022

(30) Foreign Application Priority Data

Mar. 7, 2019 (NL) ..................... 2022688

(51) Int. Cl.
| | |
|---|---|
| *A61L 27/26* | (2006.01) |
| *A61L 27/50* | (2006.01) |
| *C08F 220/28* | (2006.01) |
| *C08F 222/10* | (2006.01) |
| *C08F 2/34* | (2006.01) |

(Continued)

(52) U.S. Cl.
CPC .............. *A61L 27/26* (2013.01); *A61L 27/50* (2013.01); *C08F 220/286* (2020.02); *C08F 222/102* (2020.02); *A61L 2400/02* (2013.01); *A61L 2430/16* (2013.01); *C08F 2/34* (2013.01); *C08K 5/14* (2013.01); *C08K 5/315* (2013.01); *C08L 2203/02* (2013.01)

(58) Field of Classification Search
CPC ...... A61L 27/26; A61L 27/50; A61L 2430/16; A61L 2400/02; C08F 220/286; C08F 222/102; C08L 2203/02
USPC ......................................................... 523/113
See application file for complete search history.

(56) References Cited

U.S. PATENT DOCUMENTS

| | | |
|---|---|---|
| 6,140,438 A | 10/2000 | Ojio et al. |
| 8,466,209 B2 | 6/2013 | Akinay et al. |
| 8,685,089 B2 | 4/2014 | Kahook et al. |

(Continued)

FOREIGN PATENT DOCUMENTS

| | | |
|---|---|---|
| CA | 2916452 A1 | 3/2015 |
| CN | 103561786 A | 2/2014 |

(Continued)

*Primary Examiner* — Ruiyun Zhang
(74) *Attorney, Agent, or Firm* — Hoffmann & Baron, LLP

(57) ABSTRACT

The invention pertains to intraocular lens compositions comprising a polymeric mixture of monomers, a product comprising such compositions and uses thereof. The compositions of the inventions are completely vacuole-free, therefore resulting in a truly glistening free material. Moreover, they are soft enough to be easy to fold, have a properly tuned hardness to provide comfortable unfolding speed, require a low injection force, do not present prohibitive tackiness, and have good optical properties. Finally, the present intraocular lens compositions do not suffer from calcification.

15 Claims, 21 Drawing Sheets

(51) Int. Cl.
    *C08K 5/14*         (2006.01)
    *C08K 5/315*      (2006.01)

(56)           References Cited

U.S. PATENT DOCUMENTS

| | | |
|---|---|---|
| 2007/0225399 A1 | 9/2007 | Lowery et al. |
| 2011/0313518 A1 | 12/2011 | Laredo et al. |
| 2012/0202916 A1* | 8/2012 | Laredo .................. G02B 1/043 |
| | | 523/107 |
| 2012/0309899 A1 | 12/2012 | Akinay et al. |
| 2013/0035414 A1 | 2/2013 | Higgs et al. |
| 2013/0109779 A1* | 5/2013 | Argal .................... A61F 2/1613 |
| | | 523/113 |
| 2016/0194424 A1 | 7/2016 | Higgs et al. |

FOREIGN PATENT DOCUMENTS

| | | | |
|---|---|---|---|
| CN | 106632826 | A | 5/2017 |
| CN | 107206123 | A | 9/2017 |
| EP | 0898972 | B1 | 4/2003 |
| JP | H1156998 | A | 3/1999 |
| JP | 2013529505 | A | 7/2013 |
| JP | 2014515964 | A | 7/2014 |
| JP | 2014518644 | A | 8/2014 |
| JP | 2016536436 | A | 11/2016 |
| JP | 2019503725 | A | 4/2023 |
| WO | 2011163126 | A1 | 12/2011 |
| WO | 20212167124 | A1 | 12/2012 |

* cited by examiner

20x

100x

20x

100x

20x

100x

20x

100x

20x

100x

20x

100x

20x

100x

20x

100x

20x

100x

20x

100x

20x

100x

20x

100x

20x

100x

Alcon AcrySof (20x):

Alcon AcrySof (100x):

Hoya 255 (20x):

Hoya 255 (100x):

Avansee (20x):

Avansee (100x):

Tecnis (20x):

Tecnis (500x):

Asquelio (20x):

Asqelio (100x):

20x

100x

INTRAOCULAR LENS COMPOSITIONS

CROSS-REFERENCE TO RELATED APPLICATIONS

This application is a National Phase application of International Application No. PCT/NL2020/050146 filed Mar. 6, 2020, which claims priority to Netherlands Patent Application No. NL 2022688 filed Mar. 7, 2019, the disclosures of which are incorporated herein by reference.

BACKGROUND

The invention is in the field of intraocular lens compositions.

An intraocular lens is a lens which can be implanted in an eye, to substitute for or assist the natural lens material in its function of providing vision. An intraocular lens may be implanted in the eye in the context of for instance cataract treatment or myopia treatment.

Cataract affects the natural lens in the eye, which becomes cloudy and thereby blurs vision. In such cases, the natural lens may be replaced by an artificial lens, thereby restoring vision. Other conditions, such as myopia, may be treated by placing an intraocular lens over the natural lens, so as to change the eye's optical power.

Intraocular lens materials are well-known, and many varieties exist either commercially or experimentally. Generally, intraocular lens materials are polymerized compositions of one or more monomers. Important characteristics of such materials are clarity and stability. An important aspect of stability is the tendency of lens materials to form vacuoles with time. Vacuoles are small inclusions inside the polymeric lens materials which contain water, and are usually called glistenings. Due to the difference in refractive index between the material of the lens and the water inside the vacuoles, incident light will be diffracted in such a way to produce glare, and therefore a degraded vision.

In addition, an intraocular lens material must be flexible enough to allow folding the lens. This is important during the surgical procedure, in which the lens is implanted into the eye by being folded and placed inside a cartridge, and then injected through a nozzle in the eye through a small incision; finally, once in the eye, the lens is expected to unfold and recover its original shape. Yet the material must not be too soft, in order to avoid too quick unfolding of the lens. The unfolding time is an important characteristic of a lens material, as waiting too long for the lens to unfold during the surgical procedure is inefficient and may lead to complications, but also a lens that unfolds too quickly may cause damage to the tissues of the eye. The tackiness of the material should be low in order not to hamper unfolding of the lens inside the eye after being injected. The material needs to be not brittle and to be able to tolerate the stresses in action during the injection, where the lens will be folded and pushed through the small nozzle of the injector of about 2 mm, otherwise the lens may break in two or more pieces during the injection or deform. Finally, the optical quality of the lens needs to be high even after the lens has been injected and has recovered the original shape.

Intraocular lens materials are usually hydrophobic or hydrophilic. Hydrophilic materials have the advantage that they do not contain many vacuoles, but such materials have the disadvantage that they generally suffer from calcification, which after some unpredictable duration of time renders them unusable. Hydrophobic materials are better in that respect, as they do not suffer from calcification, but hydrophobic materials have the tendency to develop vacuoles. This in time leads to a more and more glistening lens material. In addition, hydrophobic lens materials are generally more tacky, which can potentially lead to complications during the unfolding process, as the tackiness may prevent the lens from unfolding or haptic portions stick to the optic. Many known hydrophobic lens materials are made harder to reduce glistening and reduce tackiness, but harder lens materials also unfold more slowly which compromises the efficiency of the process, and are harder to inject, which may even result in a broken injector nozzle during surgery.

The present invention improves on the known lens materials in that it provides an intraocular lens composition which is completely vacuole-free, therefore resulting in a truly glistening free material. Moreover, it is soft enough to be easy to fold, has a properly tuned hardness to provide comfortable unfolding speed, requires a low injection force, does not present prohibitive tackiness, and has good optical properties. Finally, the present intraocular lens composition does not suffer from calcification.

DETAILED DESCRIPTION

Figure 1:
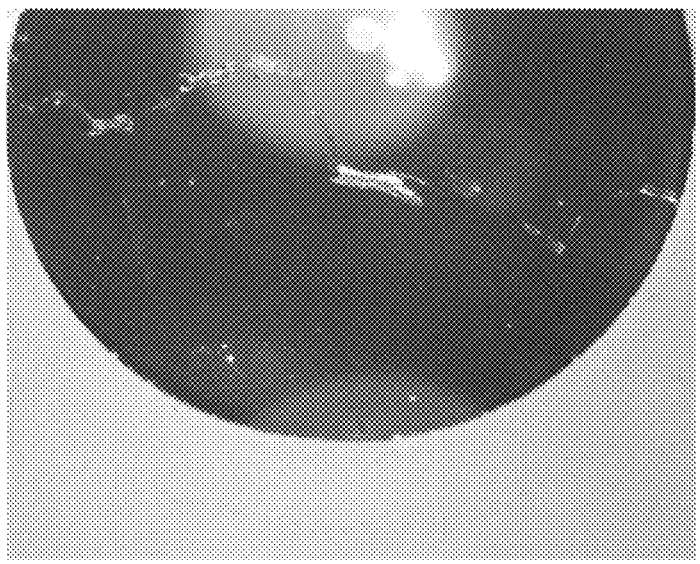
FIG. 1: Lens from example 1, 20× and 100× magnification.
Figure 1:
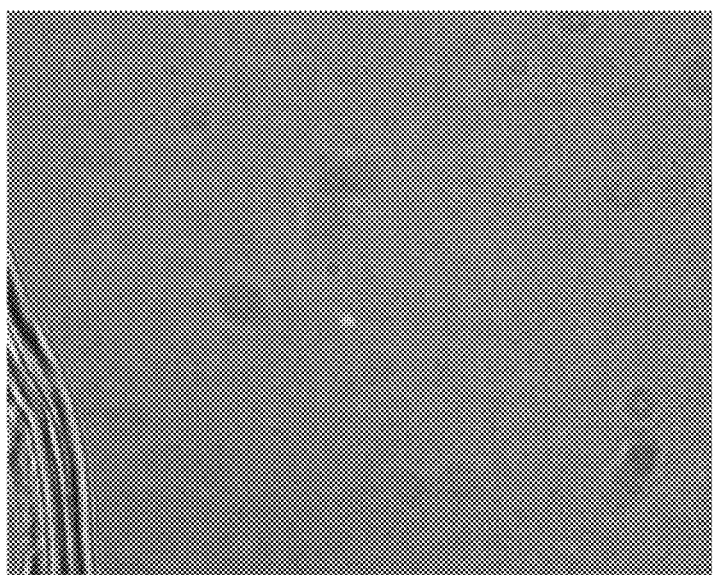
Figure 2:
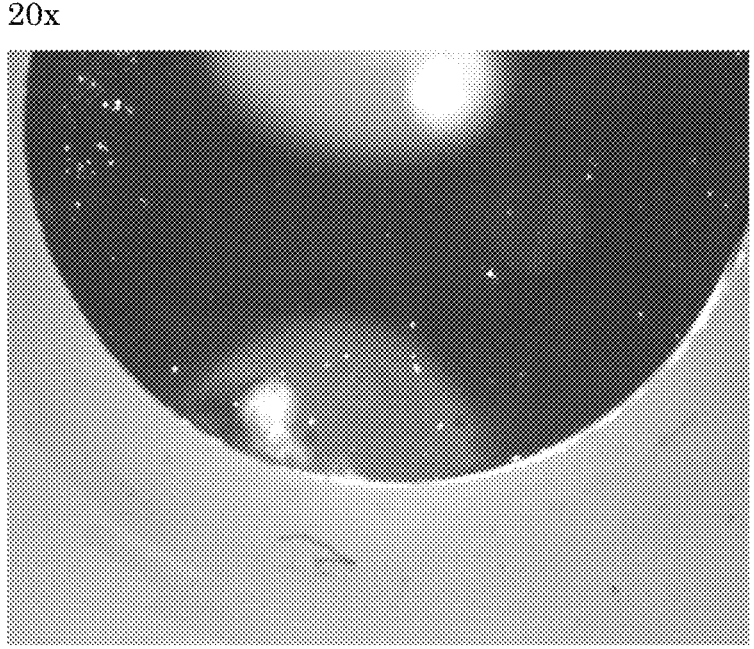
FIG. 2: Lens from example 2, 20× and 100× magnification.
Figure 2:
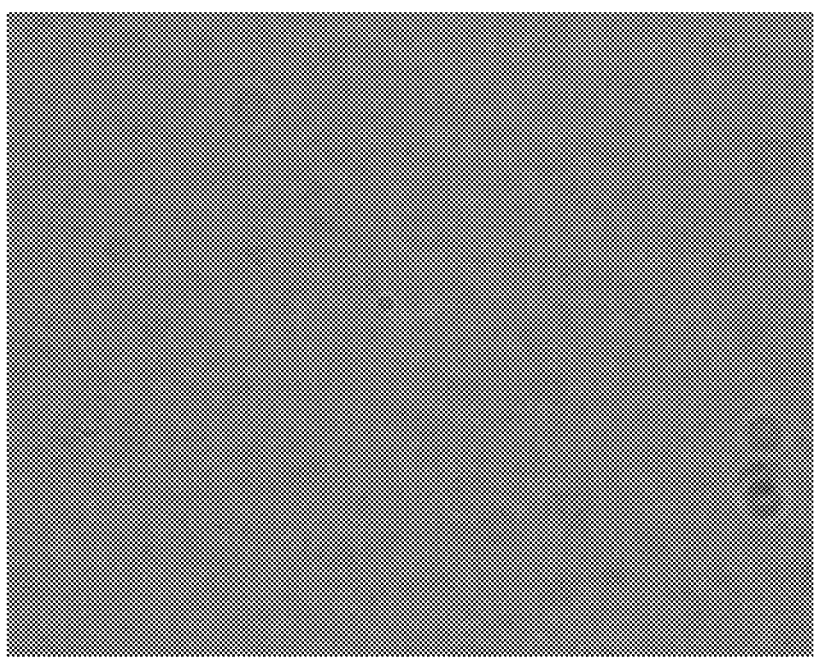
Figure 3:
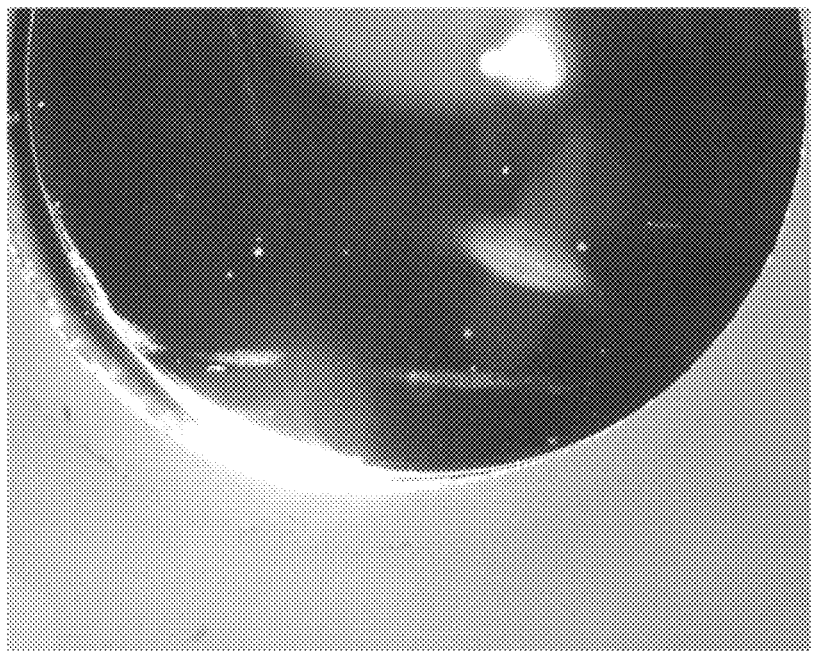
FIG. 3: Lens from example 3, 20× and 100× magnification.
Figure 3:
Figure 4:
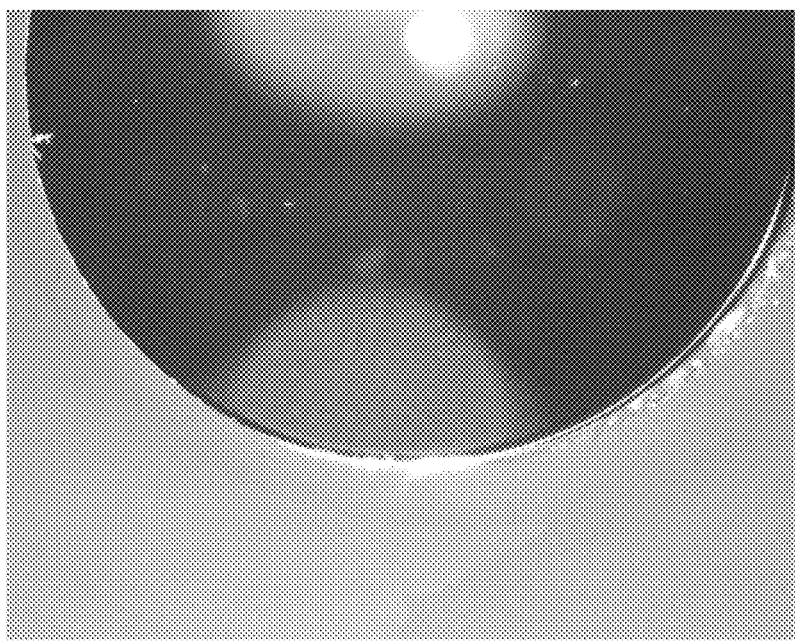
FIG. 4: Lens from example 4, 20× and 100× magnification.
Figure 4:
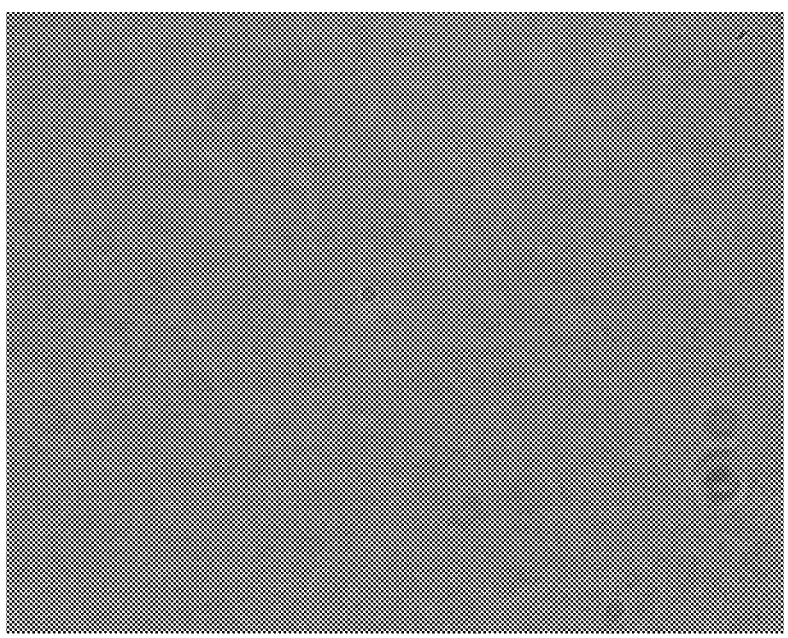
Figure 5:
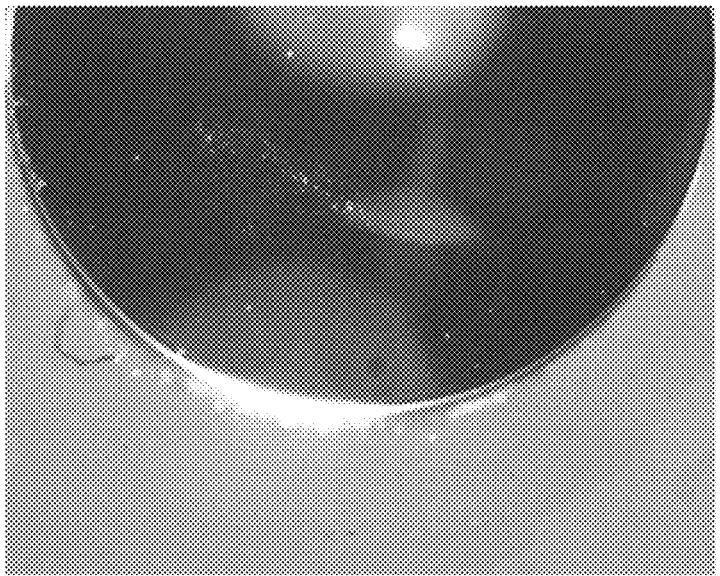
FIG. 5: Lens from example 5, 20× and 100× magnification.
Figure 5:
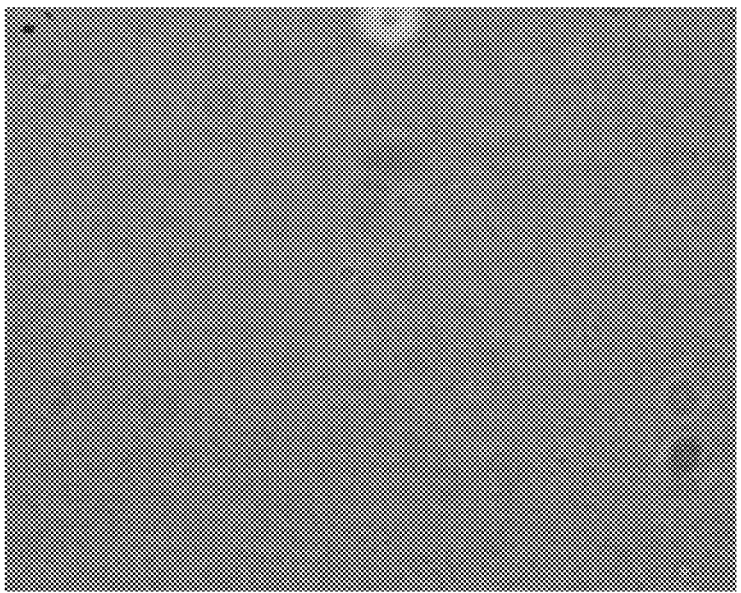
Figure 6:
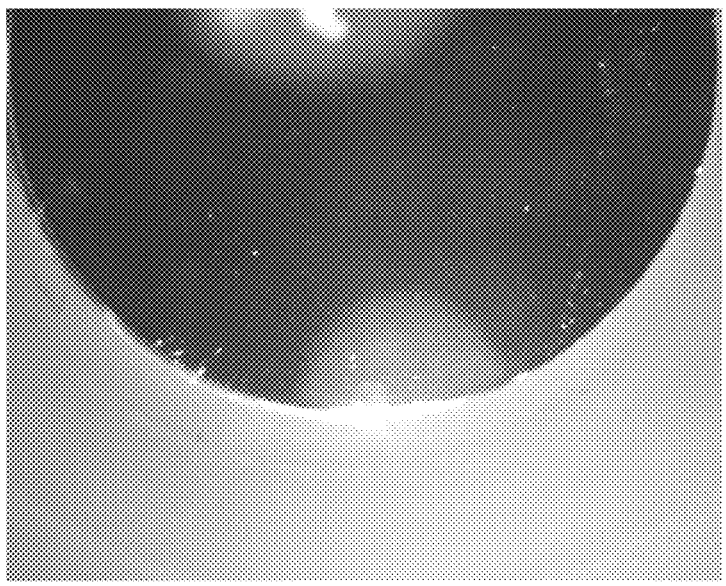
FIG. 6: Lens from example 6, 20× and 100× magnification.
Figure 6:
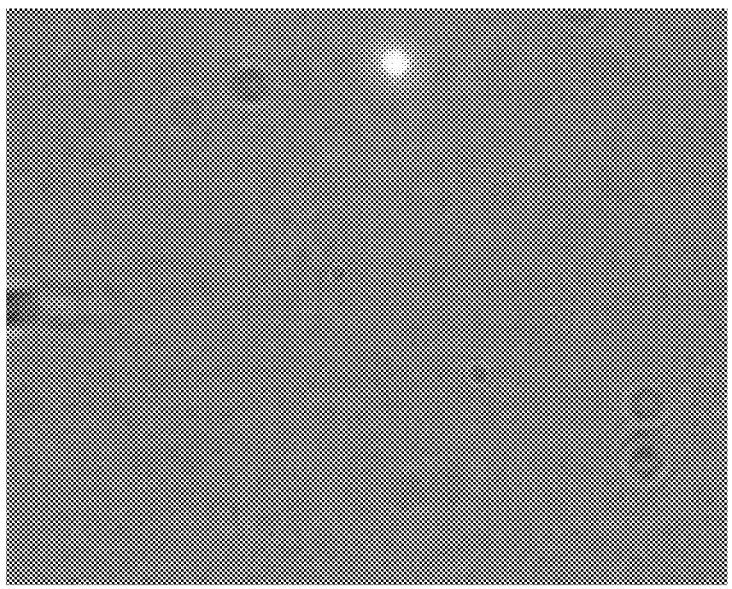
Figure 7:
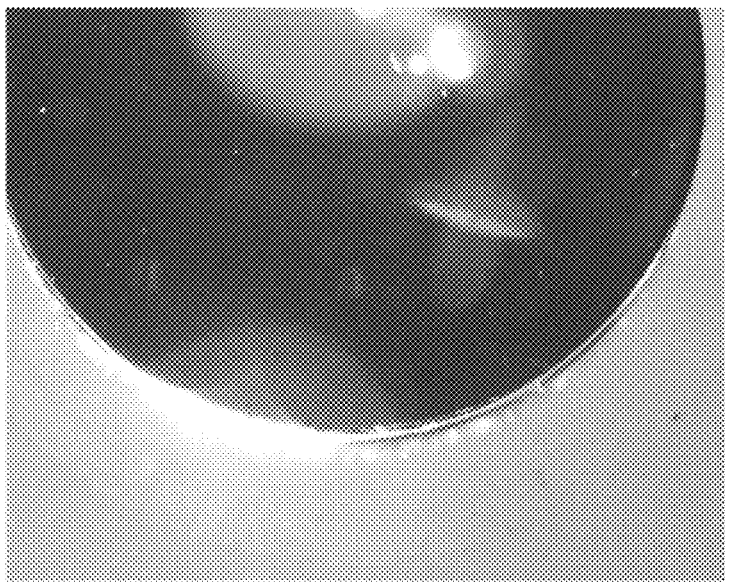
FIG. 7: Lens from example 7, 20× and 100× magnification.
Figure 7:
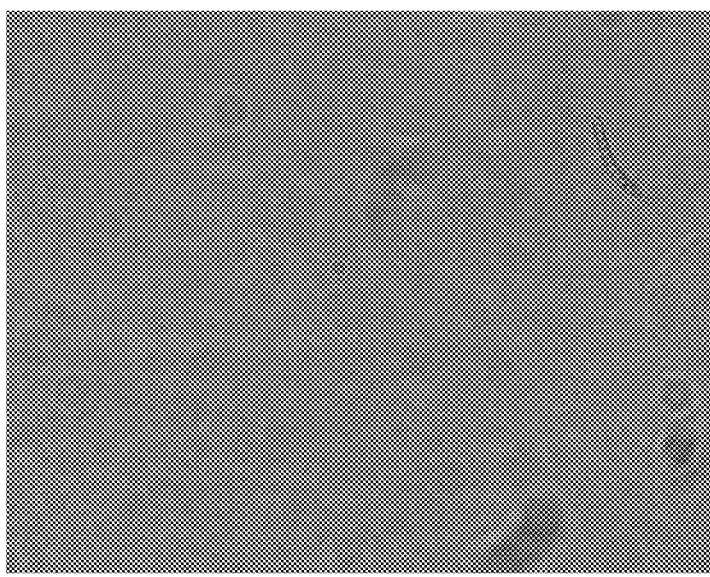
Figure 8:
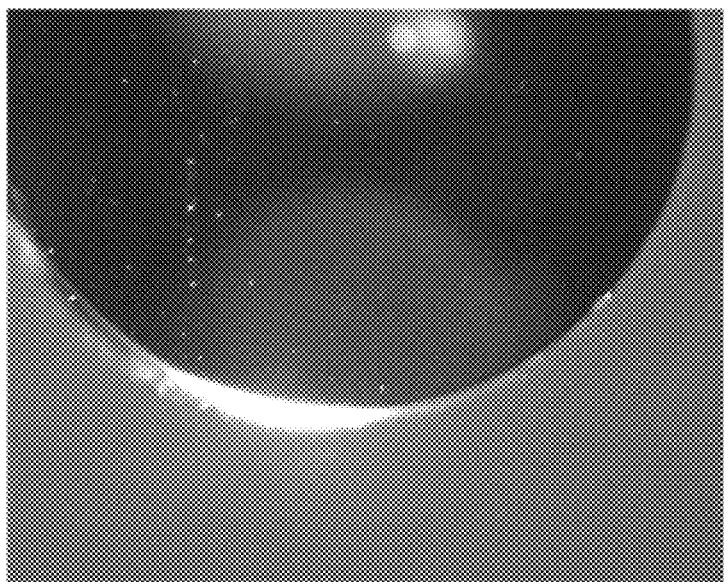
FIG. 8: Lens from example 8, 20× and 100× magnification.
Figure 8:
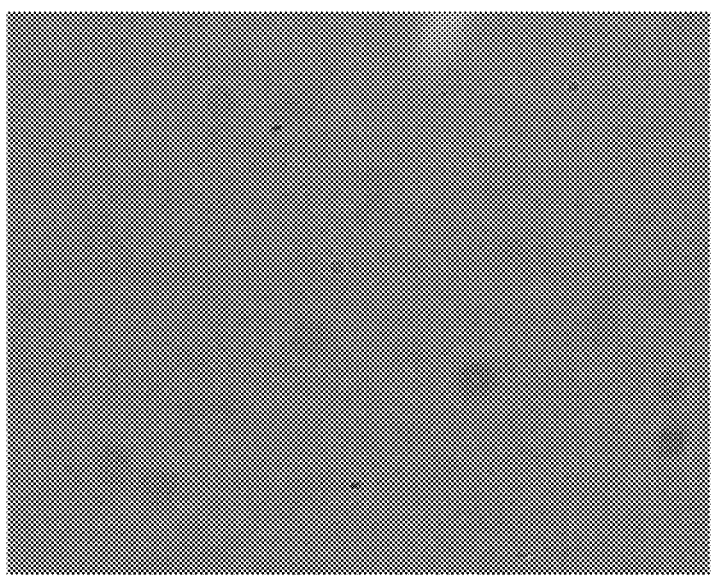

The invention is as described in claim 1. The invention provides an intraocular lens composition comprising a polymeric mixture of at least four different monomers: a short (meth)acrylate crosslinker, a long (meth)acrylate crosslinker, one or more (meth)acrylate monomers of formula (I), and either one or more C1-C4-alkyl(meth)acrylates, or a combination of a phenyl-C1-C4-alkyl(meth)acrylate and a cycloalkyl(meth)acrylate.

The present composition has the advantage over known compositions in that it provides an intraocular lens composition which is completely vacuole-free, therefore resulting in a truly glistening free material. Moreover, it is soft enough to be easy to fold, has a properly tuned hardness to provide comfortable unfolding speed, requires a low injection force, does not present prohibitive tackiness, and has good optical properties. Finally, the present intraocular lens composition does not suffer from calcification.

The intraocular lens composition may be abbreviated IOL. It is a polymeric intraocular lens composition based on at least the monomers described above, suitably polymerized. In preferred embodiments, the polymeric composition comprises at least 50 wt. %, based on the weight of the composition, of the monomers described above, suitably polymerized. In preferred embodiments, the polymeric composition comprises at least 60 wt. %, preferably at least 70 wt. % and more preferably at least 80 wt. % of the monomers described above, suitably polymerized.

The term "polymeric mixture of monomers" is interpreted as is well-known in the art, and means that the monomers comprised in the polymeric intraocular lens composition have been polymerized to provide the intraocular lens composition of the invention. Polymerized, in this context, means that at least 90%, generally more than 95% and usually essentially all monomer molecules, such as at least 99% of all monomer molecules, have undergone polymerization to yield the polymeric intraocular lens composition. If the residual total content of unreacted monomers is higher than desired, extraction with a suitable solvent can optionally be performed in order to eliminate the unreacted monomers, as it is well known in the art.

Thus, the polymeric mixture of monomers which is the intraocular lens composition is a polymeric composition, which does preferably not comprise monomers to a significant extent; rather, all monomers which have been used have become incorporated in the polymeric mixture during the polymerization reaction when preparing the intraocular lens composition. The polymeric mixture of monomers does not comprise unreacted monomers to a significant extent.

The intraocular lens composition comprises the polymeric mixture of monomers, and may furthermore comprise other conventional elements like UV and or blue light filter monomers such as described in WO1995/011279A1.

In some preferred embodiments, the intraocular lens composition consists of only the polymeric mixture, but may contain unavoidable impurities (such as for example impurities which stem from the polymerization process, most notably rests from the polymerization initiator, and degradation products).

The essential monomers to be included in the polymeric composition are (meth)acrylate monomers. The polymerization process to obtain the intraocular lens composition must therefore be adapted to allow polymerization of (meth)acrylate monomers. In preferred embodiments, the polymerization process is a radical polymerization process. Radical polymerization is well-known in the art.

The Short Crosslinker

The first essential monomer to be included in the intraocular lens composition is a short crosslinker, comprising two or more (meth)acrylate portions and a connecting portion located between the two (meth)acrylate portions and which connecting portion is connected to the (meth)acrylate portions through ester groups, wherein the longest linear atomic sequence between the oxygen atom of the ester group connecting the first (meth)acrylate portion to the connecting portion and the oxygen atom of the ester group connecting the second (meth)acrylate portion to the connecting portion is 1-11 atoms. The short crosslinker may be represented by the following formula:

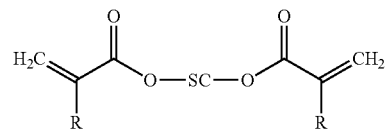

In this formula, R is H or $CH_3$, and SC represents a short connecting portion. The (meth)acrylate portions of the short crosslinker may independently be an acrylate portion or a methacrylate portion. In preferred embodiments, the short crosslinker contains two acrylate portions or two methacrylate portions. Most preferably, the short crosslinker contains two methacrylate portions (a dimethacrylate).

The connecting portion is connected to the (meth)acrylate portions of the short crosslinker through ester groups, which ester groups are located on the carbonyl group of the (meth)acrylate.

The connecting portion is defined as a portion which connects two (meth)acrylate portions through a covalently bonded sequence of atoms. The longest linear atomic sequence of the short crosslinker extends between the oxygen atom of the ester group connecting the first (meth)acrylate portion to the connecting portion and the oxygen atom of the ester group connecting the second (meth)acrylate portion to the connecting portion, and is 1-11 atoms, preferably 1-8 atoms, more preferably 2-5 atoms. Thus, the short connecting portion is represented by a linear sequence of 1-11, 1-8 or 2-5 atoms.

The longest linear atomic sequence of the short crosslinker comprises C-atoms and optionally O- and/or N-atoms, wherein the total of C-atoms exceeds the total of O- and N-atoms. In preferred embodiments, the longest linear atomic sequence of the short crosslinker comprises only C- and optionally O-atoms, wherein the total number of C-atoms exceeds the total number of O-atoms, if present. In much preferred embodiments, the ratio of C:O atoms is larger than 2:1.

The longest linear atomic sequence of the short crosslinker may comprise side groups which do not significantly affect the reactivity of the (meth)acrylate portions of the short crosslinker during the polymerization reaction. Preferably, the side groups are selected from the group consisting of $R^2$, $OR^2$, $SR^2$, $NR^2_2$, $COOR^2$ or F, wherein $R^2$ is H, alkyl, cycloalkyl, heterocycloalkyl, an aromatic portion, or any combination thereof, which $R^2$ has a molecular weight of at most 100 Da.

The short crosslinker may also comprise more than two (meth)acrylate portions, such as three or four or even more (meth)acrylate portions.

In much preferred embodiments, the short crosslinker is ethylene glycol di(meth)acrylate, propylene glycol di(meth)acrylate, butylene glycol di(meth)acrylate, diethylene glycol di(meth)acrylate, dipropylene glycol di(meth)acrylate, dibutylene glycol di(meth)acrylate, triethylene glycol di(meth)acrylate, tripropylene glycol di(meth)acrylate, tetraethylene glycol di(meth)acrylate, trimethylolpropane tri(meth)acrylate, trimethylolpropane ethoxylate tri(meth)

acrylate (with max 1 unit of ethoxylate each arm), trimethylolpropane propoxylate tri(meth)acrylate (with max 1 unit of propoxylate each arm), glycerol tri(meth)acrylate, pentaerythritol tri(meth)acrylate, glycerol ethoxylate tri (meth)acrylate (with max 1 unit of ethoxylate each arm), glycerol propoxylate tri(meth)acrylate (with max 1 unit of propoxylate each arm), pentaerythritol ethoxylate tetra(meth)acrylate (with max 1 unit of ethoxylate each arm), pentaerythritol propoxylate tetra(meth)acrylate (with max 1 unit of propoxylate each arm), di(trimethylolpropane) tetra (meth)acrylate, pentaerythritol tetra(meth)acrylate, dipentaerythritol penta(meth)acrylate, or dipentaerythritol hexa (meth)acrylate, preferably ethylene glycol di(meth)acrylate, propylene glycol di(meth)acrylate, butylene glycol di(meth) acrylate, diethylene glycol di(meth)acrylate, dipropylene glycol di(meth)acrylate, dibutylene glycol di(meth)acrylate, triethylene glycol di(meth)acrylate, tripropylene glycol di(meth)acrylate, tetraethylene glycol di(meth)acrylate, trimethylolpropane tri(meth)acrylate, glycerol tri(meth) acrylate, pentaerythritol tri(meth)acrylate, di(trimethylolpropane) tetra(meth)acrylate, pentaerythritol tetra(meth) acrylate, dipentaerythritol penta(meth)acrylate, or dipentaerythritol hexa(meth)acrylate, and more preferably ethylene glycol di(meth)acrylate, diethylene glycol di(meth) acrylate, trimethylolpropane tri(meth)acrylate, propylene glycol di(meth)acrylate, tripropylene glycol di(meth)acrylate, tetraethylene glycol di(meth)acrylate, di(trimethylolpropane) tetra(meth)acrylate, or pentaerythritol tetra(meth) acrylate.

In some embodiments, an acrylate is preferred. In alternative preferred embodiments, a methacrylate is preferred.

Preferably, the quantity of short crosslinker in the mixture of monomers is 0.1-12 wt. %, preferably 0.2-10 wt. %, more preferably 0.5-8 wt. %, based on the total monomer mixture.

In some much preferred embodiments, the quantity of short crosslinker in the mixture of monomers is 0.1-3 wt. %, preferably 0.1-2 wt. %. In other much preferred embodiments, the quantity of short crosslinker in the mixture of monomers is 2-10 wt. %, preferably 2-7 wt. %.

The Long Crosslinker

The second essential monomer to be included in the intraocular lens composition is a long crosslinker, comprising two or more (meth)acrylate portions and a connecting portion located between the two (meth)acrylate portions and which connecting portion is connected to the (meth)acrylate portions through ester groups, wherein the longest linear atomic sequence between the oxygen atom of the ester group connecting the first (meth)acrylate portion to the connecting portion and the oxygen atom of the ester group connecting the second (meth)acrylate portion to the connecting portion is 14 atoms or more. The long crosslinker may be represented by the following formula:

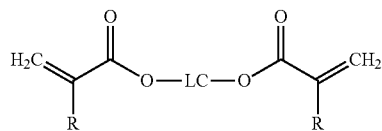

In this formula, R is H or CH$_3$, and LC represents a long connecting portion. The (meth)acrylate portions of the long crosslinker may independently be an acrylate portion or a methacrylate portion. In preferred embodiments, the long crosslinker contains two acrylate portions or two methacrylate portions.

The connecting portion is connected to the (meth)acrylate portions of the long crosslinker through ester groups, which ester groups are located on the carbonyl group of the (meth)acrylate.

The connecting portion is defined as a portion which connects two (meth)acrylate portions through a covalently bonded sequence of atoms. The longest linear atomic sequence of the connecting portion of the long crosslinker extends between the oxygen atom of the ester group connecting the first (meth)acrylate portion to the connecting portion and the oxygen atom of the ester group connecting the second (meth)acrylate portion to the connecting portion, and is 12 atoms or more, preferably at least 15 atoms, more preferably at least 20 atoms. In preferred embodiments, the long crosslinker has a longest linear atomic sequence of at most 100 atoms, preferably at most 80 atoms, more preferably at most 50 atoms, such as for example at most 30 atoms.

The longest linear atomic sequence of the long crosslinker comprises C-atoms and optionally O- and/or N-atoms, wherein the total of C-atoms exceeds the total of O- and N-atoms. In preferred embodiments, the longest linear atomic sequence of the long crosslinker comprises only C- and optionally O-atoms, wherein the total number of C-atoms exceeds the total number of O-atoms, if present. In much preferred embodiments, the ratio of C:O atoms is larger than 2:1.

The longest linear atomic sequence of the long crosslinker may comprise side groups which do not significantly affect the reactivity of the (meth)acrylate portions of the long crosslinker during the polymerization reaction. Preferably, the side groups are selected from the group consisting of $R^2$, $OR^2$, $SR^2$, $NR^2{}_2$, $COOR^2$ or F, wherein $R^2$ is H, alkyl, cycloalkyl, heterocycloalkyl, an aromatic portion, or any combination thereof, which $R^2$ has a molecular weight of at most 100 Da.

The long crosslinker may also comprise more than two (meth)acrylate portions, such as three or four or even more (meth)acrylate portions. Such long crosslinkers can be referred to as "star-shaped" long crosslinkers.

In much preferred embodiments, the long crosslinker is a poly(ethylene glycol) di(meth)acrylate, a poly(propylene glycol) di(meth)acrylate, a poly(butylene glycol) di(meth) acrylate, a poly(pentylene glycol) di(meth)acrylate, trimethylolpropane ethoxylate tri(meth)acrylate (with enough ethoxylate units to form a connecting part of at least 12 atoms), trimethylolpropane propoxylate tri(meth)acrylate (with enough propoxylate units to form a connecting part of at least 12 atoms), glycerol ethoxylate tri(meth)acrylate (with enough ethoxylate units to form a connecting part of at least 12 atoms), glycerol propoxylate tri(meth)acrylate (with enough propoxylate units to form a connecting part of at least 12 atoms), pentaerythritol ethoxylate tetra(meth) acrylate (with enough ethoxylate units to form a connecting part of at least 12 atoms), pentaerythritol propoxylate tetra (meth)acrylate (with enough propoxylate units to form a connecting part of at least 12 atoms), preferably a poly (ethylene glycol) di(meth)acrylate, a poly(propylene glycol) di(meth)acrylate, a trimethylolpropane ethoxylate tri(meth) acrylate (with enough ethoxylate units to form a connecting part of at least 12 atoms) or a trimethylolpropane propoxylate tri(meth)acrylate (with enough propoxylate units to form a connecting part of at least 12 atoms).

In some embodiments, an acrylate is preferred. In alternative preferred embodiments, a methacrylate is preferred.

In preferred embodiments, the long crosslinker has a molecular weight of between 340 and 5000 Da, preferably between 346 and 3000 Da, more preferably between 350 and 1500 Da, most preferably 400-1000 Da.

Preferably, the quantity of long crosslinker in the mixture of monomers is 0.5-25 wt. %, preferably 1-25 wt. %, more preferably 2-20 wt. %, more preferably 2-10 wt. %, based on the total monomer mixture.

In some much preferred embodiments, the quantity of long crosslinker in the mixture of monomers is 1-15 wt. %, preferably 2-12 wt. %. In other much preferred embodiments, the quantity of long crosslinker in the mixture of monomers is 1-20 wt. %, preferably 7-18 wt. %.

The One or More (Meth)Acrylate Monomers of Formula (I)

A third essential monomer in the polymeric intraocular lens composition is one or more (meth)acrylate monomers of formula (I):

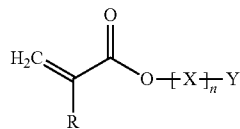

wherein:
X is —(C1-C4 alkyl)-O—, —(C1-C4 alkyl)-S—, —(C1-C4 alkyl)-N— or a C1-C8 alkyl group, which C1-C8 alkyl group comprises a cycloalkyl and wherein one of the C-atoms is replaced by a heteroatom selected from the group of O, S and N;
Y is absent or —C1-C4 alkyl;
n is 1-6;
R is H or $CH_3$.

In formula (I), the alkyl portions in X and Y may be linear, branched or cyclic, but preferably they are linear. Optionally, the alkyl portions may be substituted with groups which do not affect the reactivity of the (meth)acrylate portion, such as e.g. fluoro groups. In preferred embodiments X is —(C1-C4 alkyl)-O— or —(C1-C4 alkyl)-S—, more preferably X is —(C1-C4 alkyl)-O—. In preferred embodiments, n is 1 or 2.

In preferred embodiments, the (meth)acrylate monomer of formula (I) is a methoxymethyl(meth)acrylate, a methoxyethyl(meth)acrylate, a methoxypropyl(meth)acrylate, a methoxybutyl(meth)acrylate, a ethoxymethyl(meth) acrylate, a ethoxyethyl(meth)acrylate, a ethoxypropyl(meth) acrylate, a ethoxybutyl(meth)acrylate, a propyloxymethyl (meth)acrylate, a propyloxyethyl(meth)acrylate, a propyloxypropyl(meth)acrylate, a propyloxybutyl(meth) acrylate, a butoxymethyl(meth)acrylate, a butoxyethyl (meth)acrylate, a butoxypropyl(meth)acrylate or a butoxybutyl(meth)acrylate. In some embodiments, an acrylate is preferred. In alternative preferred embodiments, a methacrylate is preferred.

In more preferred embodiments, the (meth)acrylate monomer of formula (I) is a methoxyethyl(meth)acrylate, a methoxypropyl(meth)acrylate, a ethoxyethyl(meth)acrylate, a methoxyethoxyethyl (meth)acrylate, a di(ethylene glycol) ethyl ether (meth)acrylate or a triethylene glycol methyl ether (meth)acrylate or a ethoxypropyl(meth)acrylate, or a propyloxyethyl(meth)acrylate.

In much preferred embodiments, the (meth)acrylate monomer of formula (I) is a methoxyethyl acrylate or a methoxyethyl methacrylate. Most preferably, the one or more (meth)acrylate monomers of formula (I) comprises methoxyethyl methacrylate, methoxyethyl acrylate, ethoxyethyl methacrylate, ethoxyethylacrylate, methoxyethoxyethyl methacrylate, methoxyethoxyethyl acrylate, di(ethylene glycol) ethyl ether acrylate and triethylene glycol methyl ether methacrylate. In some embodiments a mixture of a methacrylate and an acrylate of the same (meth)acrylate monomers of formula (I) is preferred. In some preferred embodiments a mixture of a methoxyethyl acrylate and a methoxyethyl methacrylate is preferred.

In preferred embodiments, the (total) quantity of the one or more (meth)acrylate monomers of formula (I) in the mixture of monomers is 15-90 wt. %, preferably 18-85 wt. %.

In some much preferred embodiments, the total quantity of the (meth)acrylate monomer of formula (I) in the mixture of monomers is 35-90 wt. %, preferably 42-83 wt. %, based on the total monomer mixture. In other much preferred embodiments, the quantity of (meth)acrylate monomer of formula (I) in the mixture of monomers is 15-55 wt. %, preferably 18-45 wt. %.

The Fourth Monomer

A fourth essential monomer in the polymeric intraocular lens composition is either one or more C1-C4-alkyl(meth) acrylates, or alternatively a combination of a phenyl-C1-C4-alkyl(meth)acrylate and a cycloalkyl(meth)acrylate. The total quantity of alkyl(meth)acrylate or the combination of phenylalkyl(meth)acrylate and cycloalkyl(meth)acrylate is preferably 5-70 wt. %, more preferably 5-35 wt. %, based on the total monomer mixture.

The One or More C1-C4-Alkyl(Meth)Acrylates

The one or more C1-C4-alkyl(meth)acrylates can be represented by formula II:

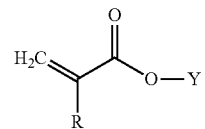

wherein:
Y is —C1-C4 alkyl;
R is H or $CH_3$.

In formula II, the alkyl portions in Y may be linear, branched or cyclic, but preferably they are linear. Optionally, the alkyl portions may be substituted with groups which do not affect the reactivity of the (meth)acrylate portion, such as e.g. fluoro groups.

In preferred embodiments, the C1-C4-alkyl(meth)acrylate can be methyl (meth)acrylate, ethyl (meth)acrylate, propyl (meth)acrylate, such as n-propyl or isopropyl (meth)acrylate or butyl (meth)acrylate, such as n-butyl, sec-butyl, isobutyl tert-butyl or cyclobutyl-(meth)acrylate. Among these (meth) acrylates, methacrylates are preferred. In particularly preferred embodiments, the C1-C4-alkyl(meth)acrylate is methyl (meth)acrylate, ethyl (meth)acrylate, propyl (meth) acrylate, butyl (meth)acrylate or tert-butyl (meth)acrylate, preferably methyl methacrylate, ethyl methacrylate, propyl methacrylate, butyl methacrylate or tert-butyl acrylate, most preferably methyl methacrylate, ethyl methacrylate, propyl methacrylate or butyl methacrylate.

The quantity of the C1-C4-alkyl(meth)acrylate in the mixture of monomers, if present, is preferably 5-75 wt. %, more preferably 15-70 wt. %, based on the total monomer mixture.

The Phenyl-C1-C4-Alkyl(Meth)Acrylate

The phenyl-C1-C4-alkyl(meth)acrylate, if present, is of formula (III):

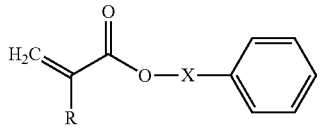

(III)

wherein:
X is absent or —C1-C4 alkyl;
R is H or $CH_3$.

In formula III, the phenyl portion may optionally be substituted with groups which do not affect the reactivity of the (meth)acrylate portion, such as for example C1-C6 (cyclo)alkyl groups, C1-C6 (cyclo)alkoxy groups or fluoro groups. In preferred embodiments, the phenyl-C1-C4-alkyl (meth)acrylate can be phenylmethyl (meth)acrylate (also referred to as benzyl (meth)acrylate), phenyl (meth)acrylate, 1-phenylethyl(meth)acrylate, 2-phenylethyl(meth)acrylate, 1-phenylpropyl(meth)acrylate, 2-phenylpropyl(meth)acrylate, 3-phenylpropyl(meth)acrylate, phenylcyclopropyl (meth)acrylate, 1-phenylbutyl(meth)acrylate, 2-phenylbutyl (meth)acrylate, 3-phenylbutyl(meth)acrylate, 4-phenylbutyl (meth)acrylate or phenylcyclobutyl(meth)acrylate.

In much preferred embodiments, the phenyl-C1-C4-alkyl (meth)acrylate is phenyl(meth)acrylate, phenylmethyl (meth)acrylate, phenylethyl(meth)acrylate. The quantity of the phenyl-C1-C4-alkyl(meth)acrylate in the mixture of monomers, if present, is preferably 5-40 wt. %, more preferably 8-33 wt. %, based on the total monomer mixture.

The Cycloalkyl(Meth)Acrylate

The cycloalkyl(meth)acrylate, if present, is of formula (IV)

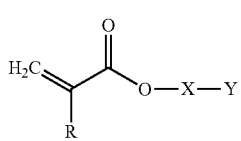

(IV)

wherein:
X is absent, a C1-C5 alkyl group, or a —[(C1-C4 alkyl)-O]$_n$— group wherein n is 1-8;
Y is a C3-C18 alkyl group comprising at least one cycloalkyl portion, which C3-C18 alkyl group optionally comprises one or more heteroatoms selected from the group of O and N;
R is H or $CH_3$.

In formula IV, the alkyl portions in X may be linear, branched or cyclic, but preferably they are linear. Optionally, the alkyl portions may be substituted with groups which do not affect the reactivity of the (meth)acrylate portion, such as e.g. fluoro groups.

Preferably, X is absent, methylene, ethylene, propylene, butylene or pentylene, and more preferably X is absent, methylene or ethylene. Most preferably, X is absent. Y is a C3-C18 alkyl group comprising at least one cycloalkyl portion, in which optionally one or more C-atoms of the alkyl group may be replaced by O- and/or N-atoms, preferably O-atoms. Thus, the total number of C, O and/or N atoms in group Y does not exceed 18. If present, the O and N atoms are preferably not located in the cycloalkyl portion.

Preferably, Y comprises a monocyclic ring system such as cyclopropyl, cyclobutyl, cyclopentyl, cyclohexyl, cycloheptyl, cyclooctyl, or a bicyclic or tricyclic alkyl group comprising any combination of these monocyclic systems. Particularly preferred bi- or tricyclic systems are norbornyl, isobornyl, or adamantyl.

Y may further comprise a linear or branched alkyl portion, possibly comprising heteroatoms O and/or N, which is located between X and the cycloalkyl portion. Optionally, the cycloalkyl portion can be further substituted with alkyl groups, fluoro groups, hydroxyl (OH) groups or amino ($NH_2$) groups, as well as alkyl substituted derivatives of amino- or hydroxy-substituted cycloalkyl portions (i.e. an ether or secondary or tertiary amine).

In preferred embodiments, Y is a cycloalkyl group, more preferably a C3-C10 cycloalkyl group.

In much preferred embodiments, the cycloalkyl(meth) acrylate is a cyclopentyl(meth)acrylate, a cyclohexyl(meth) acrylate, a cycloheptyl(meth)acrylate, a norbornyl(meth) acrylate, an isobornyl(meth)acrylate or an adamantyl (meth) acrylate. Among these, methacrylates are preferred. Alternatively preferred are acrylates.

The quantity of the cycloalkyl(meth)acrylate in the mixture of monomers, if present, is preferably 10-55 wt. %, more preferably 14-45 wt. %, based on the total monomer mixture.

Optional Monomers in the Mixture of Monomers

As mentioned, the polymeric composition preferably comprises at least 50 wt. %, based on the weight of the composition, of the monomers described above, suitably polymerized. In preferred embodiments, the polymeric composition comprises at least 60 wt. %, preferably at least 70 wt. % and more preferably at least 80 wt. % of the monomers described above, suitably polymerized. Other conventional monomers than those listed above may thus be present to a considerable extent. These other conventional monomers can be chosen from all (meth)acrylic and vinylic monomers conventional in the field of intraocular lenses, not falling in one of the above essential classes.

In a preferred embodiment, the mixture of monomers further comprises a UV light-filtering chromophore ("UV-blocker" or "UV filter") in a quantity suitable to absorb at least 50%, preferably at least 75%, more preferably at least 85% of optical radiation with a wavelength between 350 and 400 nm, preferably a benzotriazole-substituted methacrylate. Examples of such UV filter chromophores are 2-[3-(2H-benzotriazol-2-yl)-4-hydroxyphenyl]ethyl methacrylate (CAS 96478-09-0), and 2-(4-Benzoyl-3-hydroxyphenoxy)ethyl acrylate (CAS 16432-81-8).

In case the composition comprises a UV light-filtering chromophore as defined, the quantity of this monomer is preferably between 0.1 and 2 wt. % of the mixture of monomers, preferably 0.2-1 wt. %, more preferably 0.4-0.8 wt. %.

In a further preferred embodiment, the mixture of monomers further comprises a blue light-filtering chromophore ("blue light filter") in a quantity suitable to absorb at least 50%, preferably at least 75%, more preferably at least 85% of optical radiation with a wavelength between 400 and 500 nm. Examples of such blue light filter chromophores are the polymerizable yellow dyes described in WO 1995/011279A1. In case the composition comprises a blue light-filtering chromophore as defined, the quantity of this monomer is preferably between 0.1 and 2 wt. % of the mixture of monomers, preferably 0.2-1 wt. %, more preferably 0.4-0.8 wt. %.

PREFERRED EMBODIMENTS

A preferred intraocular lens composition according to the invention comprises:
- 0.1-12 wt. %, preferably 0.5-8 wt. %, of the short crosslinker;
- 1-25 wt. %, preferably 2-10 wt. %, of the long crosslinker;
- 15-90 wt. %, preferably 18-85 wt. %, of the one or more (meth)acrylate monomers of formula (I);
- 5-75 wt. %, preferably 15-70 wt. %, of the one or more C1-C4-alkyl(meth)acrylates of formula (II), if present;
- 5-40 wt. %, preferably 8-33 wt. %, of the phenyl-C1-C4-alkyl(meth)acrylate of formula (III), if present;
- 10-55 wt. %, preferably 14-45 wt. %, of the cycloalkyl (meth)acrylate of formula (IV), if present; and
- optionally 0.1 and 2 wt. % of a UV light-filtering chromophore and/or 0.1 and 2 wt. % of a blue light-filtering chromophore, wherein the wt. % is the wt. % in the mixture of monomers, based on the total monomer mixture.

In much preferred embodiments, the intraocular lens composition comprises a polymeric mixture of the monomers
- 15-90 wt. %, preferably 18-85 wt. %, of the one or more (meth)acrylate monomers of formula (I);
- 5-75 wt. %, preferably 15-70 wt. %, of the one or more C1-C4-alkyl(meth)acrylates of formula (II);
- 1-25 wt. %, preferably 2-10 wt. %, of the long crosslinker;
- 0.1-12 wt. %, preferably 0.5-8 wt. %, of the short crosslinker.

Such mixture is referred to as embodiment A. In much preferred embodiments, a UV and/or blue light-filtering chromophore as defined above is included in embodiment A.

In alternative much preferred embodiments, the intraocular lens composition comprises a polymeric mixture of the monomers
- 15-90 wt. %, preferably 18-85 wt. %, of the one or more (meth)acrylate monomers of formula (I);
- 5-40 wt. %, preferably 8-33 wt. %, of the phenyl-C1-C4-alkyl(meth)acrylate of formula (III);
- 10-55 wt. %, preferably 14-45 wt. %, of the cycloalkyl (meth)acrylate of formula (IV);
- 1-25 wt. %, preferably 2-10 wt. %, of the long crosslinker;
- 0.1-12 wt. %, preferably 0.5-8 wt. %, of the short crosslinker.

Such mixture is referred to as embodiment B. In much preferred embodiments, a UV and/or blue light-filtering chromophore as defined above is included in embodiment B.

Further preferred compositions according to the invention comprise a polymeric mixture of the monomers of examples 1-13. For each exemplary composition in Examples 1-13, the listed monomer can be present in a quantity which deviates slightly from the used quantity of that monomer in the example. A slight deviation, in this context, means that the quantity of monomer can be from 5 wt. % lower to 5 wt. % higher than the indicated quantity in the example, preferably from 2 wt. % lower to 2 wt. % higher than the exemplary quantity, more preferably from 1 wt. % lower to 1 wt. %, more preferably from 0.5 wt. % lower to 0.5 wt. % higher. Thus, for each lens composition according to the invention in the examples, the listed monomers may be present in the listed quantity ±5 wt. %, preferably ±2 wt. %, more preferably ±1 wt. %, most preferably ±0.5 wt. %. Such slight deviations do not affect the characteristics of the obtained lens. The invention thus provides a lens material, characterized by the individual examples according to the invention.

Characteristics of the Present Polymeric Composition

The intraocular lens compositions defined herein are completely vacuole-free. This sets the present compositions apart from the compositions of the prior art. In the prior art, the tendency of a composition to form vacuoles in time is determined by aging the composition for a specific time at a specific temperature. Common aging temperatures as published in literature were for instance 37 or 40° C. (for example: in WO2015084788A1, U.S. Pat. No. 8,449,610B2 the aging temperature was 45° C. for 1 day, then room temperature for 1-2 hours; in EP1857477B1 a temperature of 33° C. is used; in Biomedical Optic Express, 4, 8, 2013, 1294-1304 a temperature of 35° C. for 8 h is used; in J Cataract Refract Surg 2004, 30, 1768-1772 a maximum temperature of 41° C. was used; in WO2012106118A2 a temperature of 50° C. is used, but the specimens are inspected without a step at room temperature); aging time is for instance 1 day or a few hours. In prior art experiments on vacuole formation, the aging temperature was never as high as 50° C. or higher, followed by cooling at room temperature.

It is known and accepted that aging the composition at higher temperatures mimics an accelerated aging process under in vivo conditions. Thus, the tendency of a material to form vacuoles after years of use can be mimicked by aging at higher temperature for much shorter periods. The present test consists in aging the compositions at 50° C. for 16 hours or longer in a 0.9% NaCl aqueous solution. These conditions are significantly harsher than previously done in the art, and therefore this method is much more sensitive in showing vacuole formation after prolonged use in vivo.

Comparison using the present standardized and more stringent test conditions of a variety of known intraocular lens compositions shows that known compositions are prone to vacuole formation and/or cloudiness formation. The present compositions however are and remain completely vacuole-free, also using the present harsher test conditions described above. This makes the present compositions exceptionally suitable for use as a foldable implantable ophthalmic device in eye surgery, such as in the treatment of cataract and refractive surgery, e.g. in the treatment of myopia, due to the fact that vacuoles formation is totally prevented.

The intraocular lens compositions defined herein have a water uptake of preferably less than 10 wt. %, more preferably less than 5 wt %. The water uptake can be measured by weight, according to the following procedure: an amount of lenses (usually between 10 and 20) are allowed to fully hydrate, and their weight is measured. Next, the lenses are dried in a vacuum oven until the weight stabilizes. Subsequently, the water uptake (in percentage) is measured according to the formula $(W_{wet}-W_{dry})/W_{dry}*100\%$, where Wet is the weight of the hydrated lenses (the hydrated lenses are of course dried from the residual water on their surface), and $W_{dry}$ is the weight of the lenses after drying completely in the vacuum oven.

Figure 9:
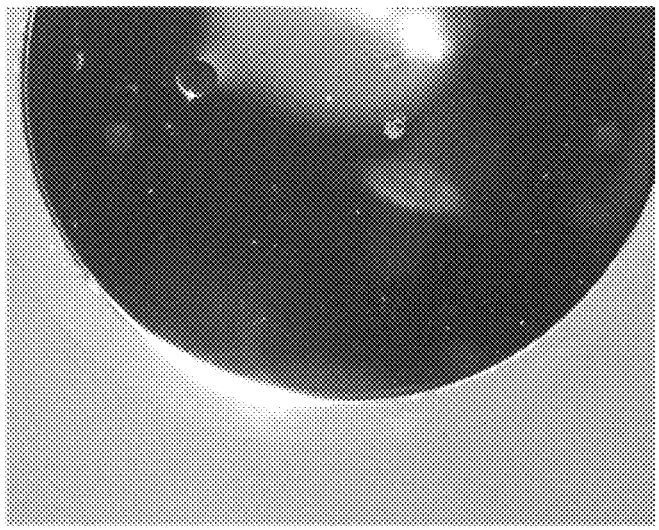
FIG. 9: Lens from example 9, 20× and 100× magnification.
Figure 9:
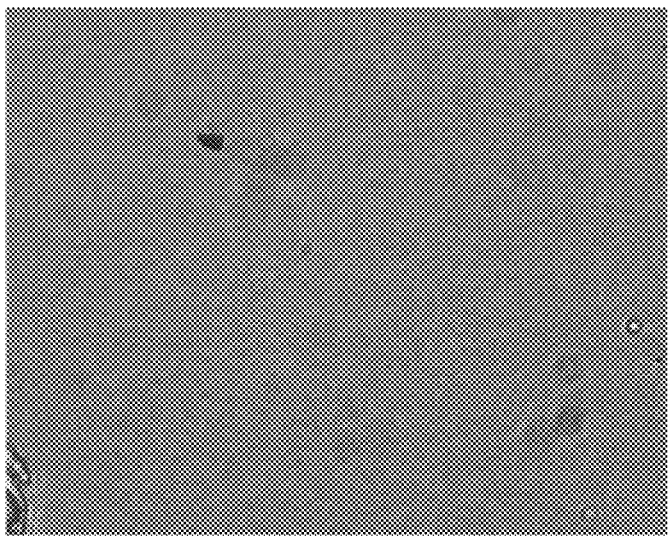
Figure 10:
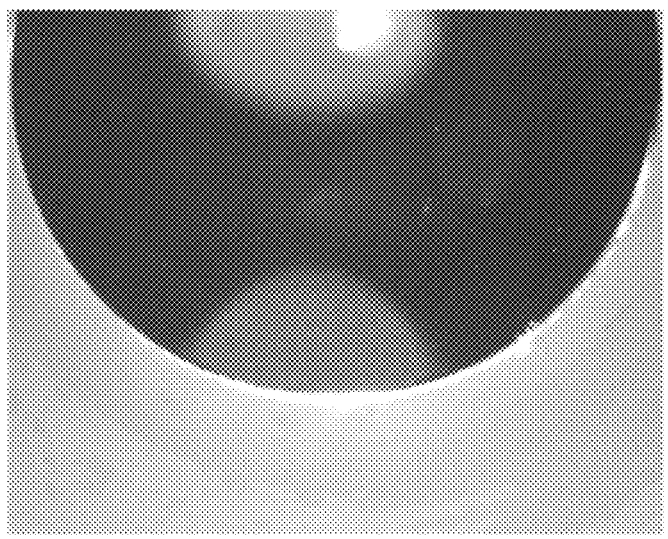
FIG. 10: Lens from example 10, 20× and 100× magnification.
Figure 10:
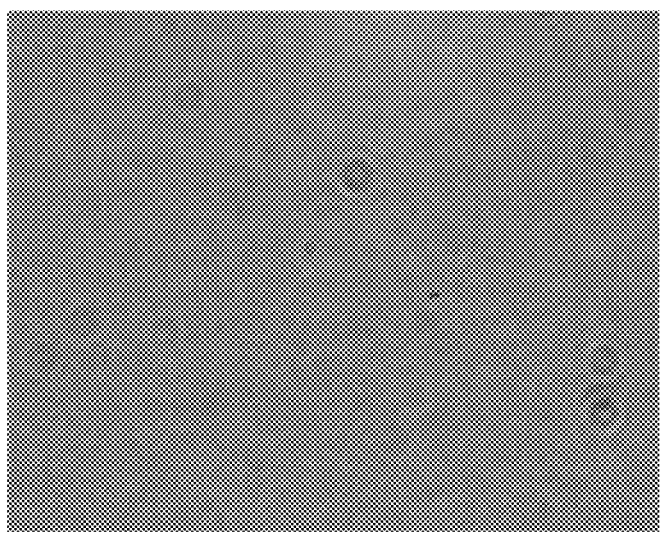
Figure 11:
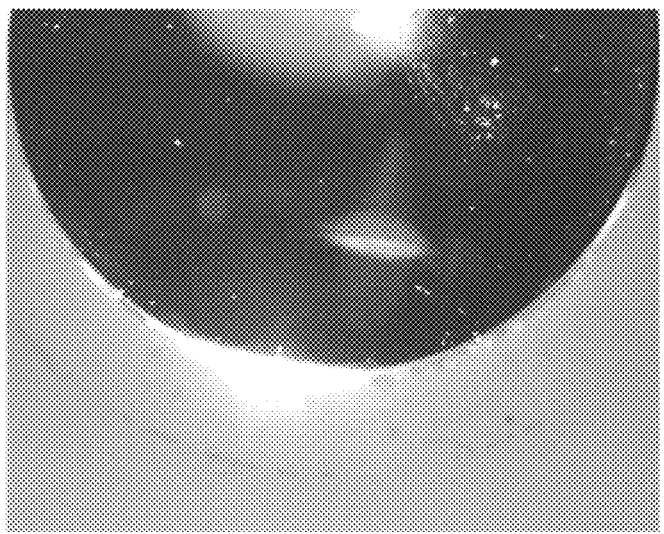
FIG. 11: Lens from example 11, 20× and 100× magnification.
Figure 11:
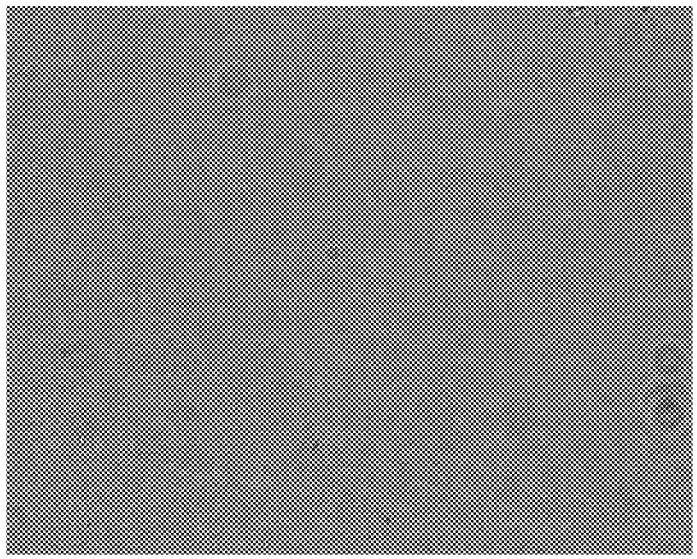
Figure 12:
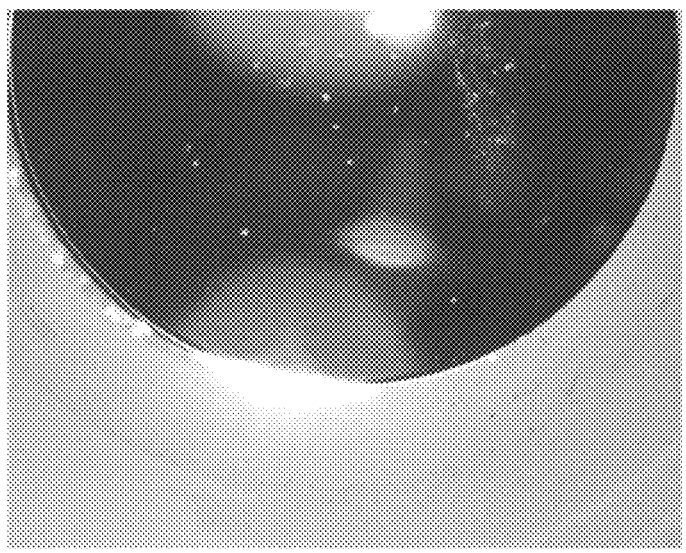
FIG. 12: Lens from example 12, 20× and 100× magnification.
Figure 12:
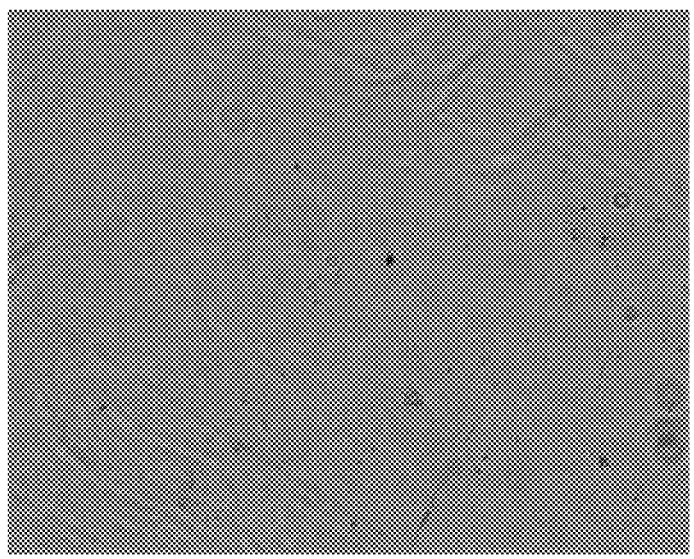
Figure 13:
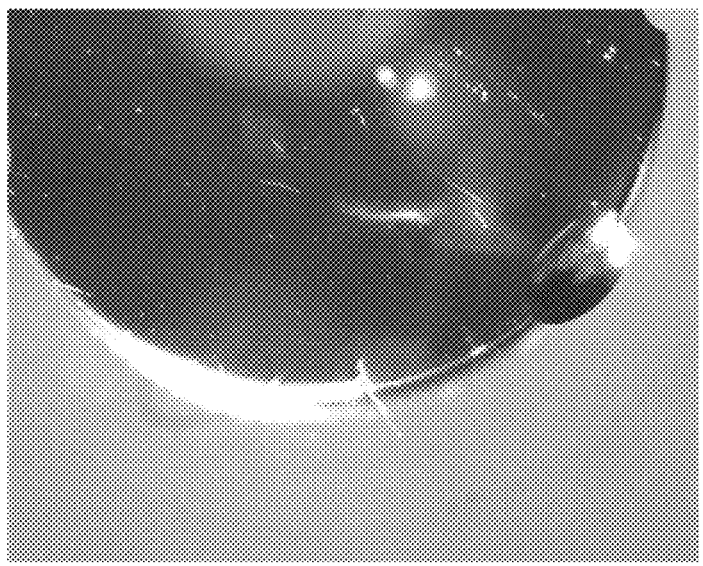
FIG. 13: Lens from example 13, 20× and 100× magnification.
Figure 13:
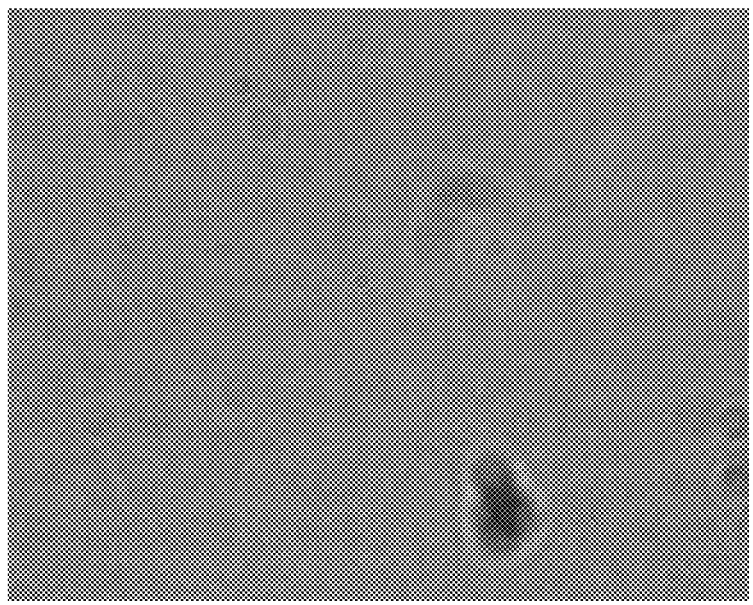
Figure 14:
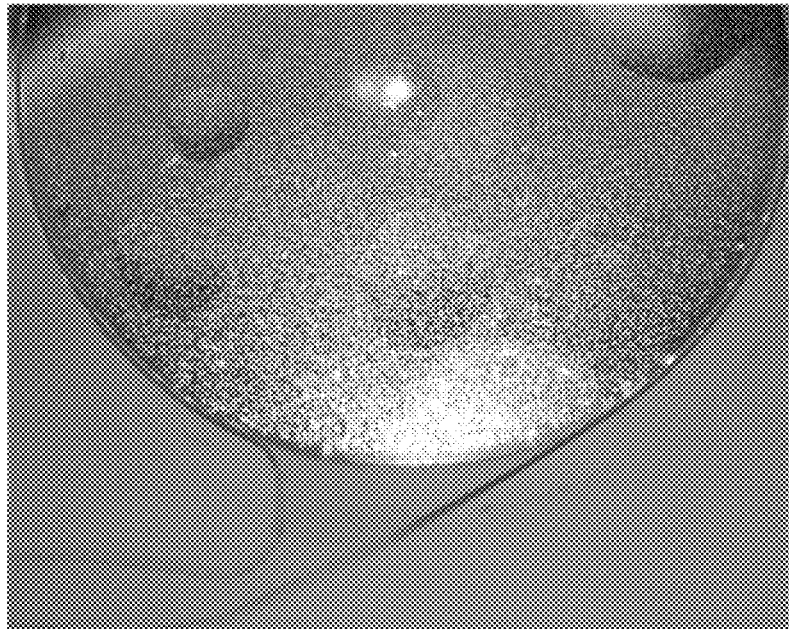
FIG. 14: Alcon AcrySof lens, 20× and 100× magnification.
Figure 14:
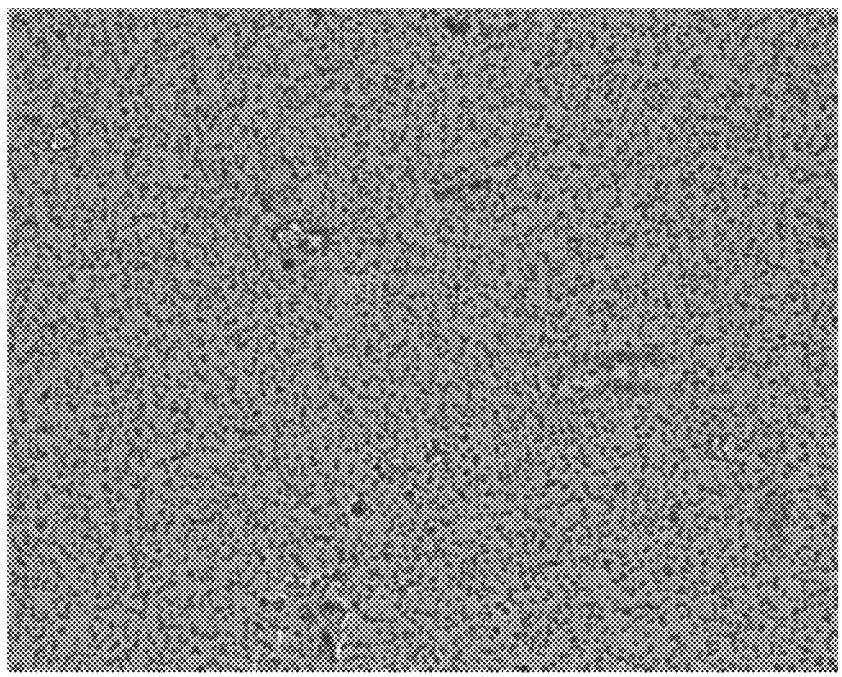
Figure 15:
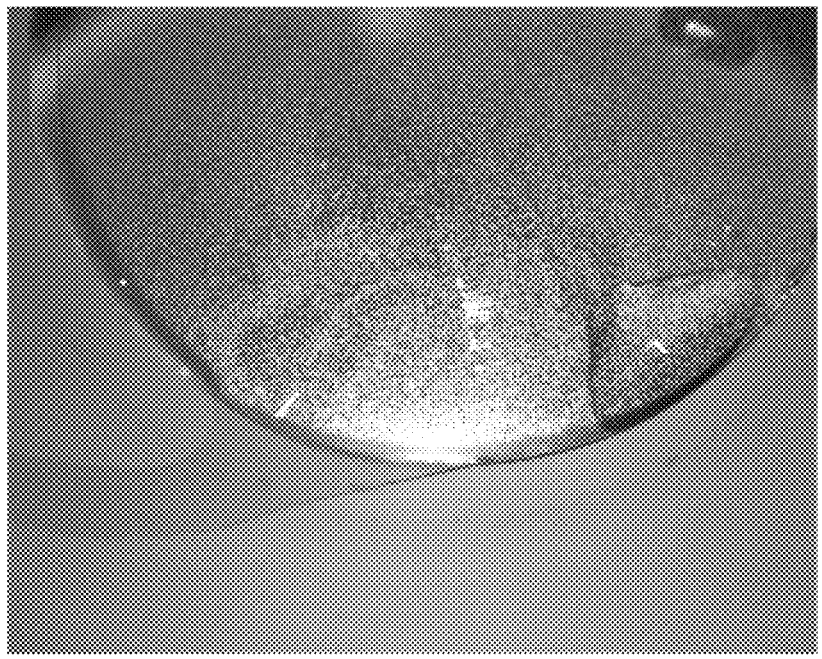
FIG. 15: Hoya 255 lens, 20× and 100× magnification.
Figure 15:
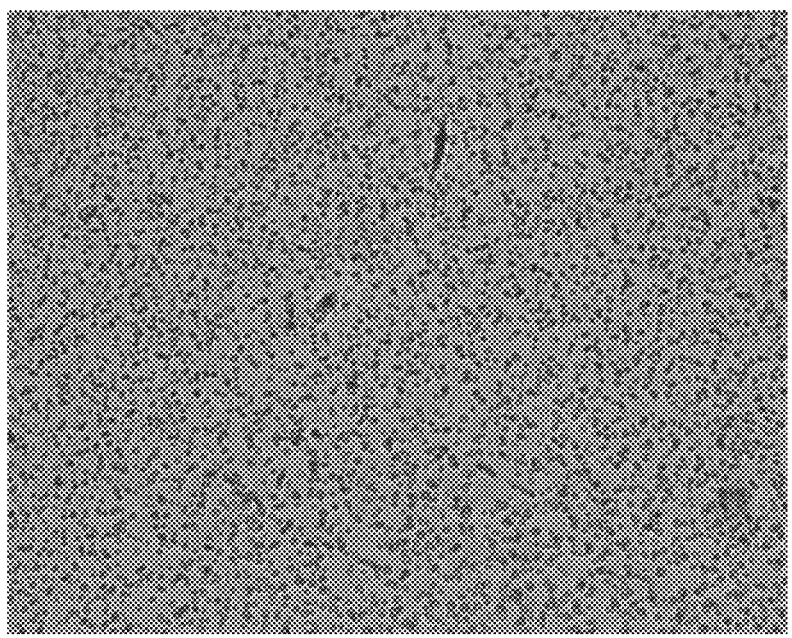
Figure 16:
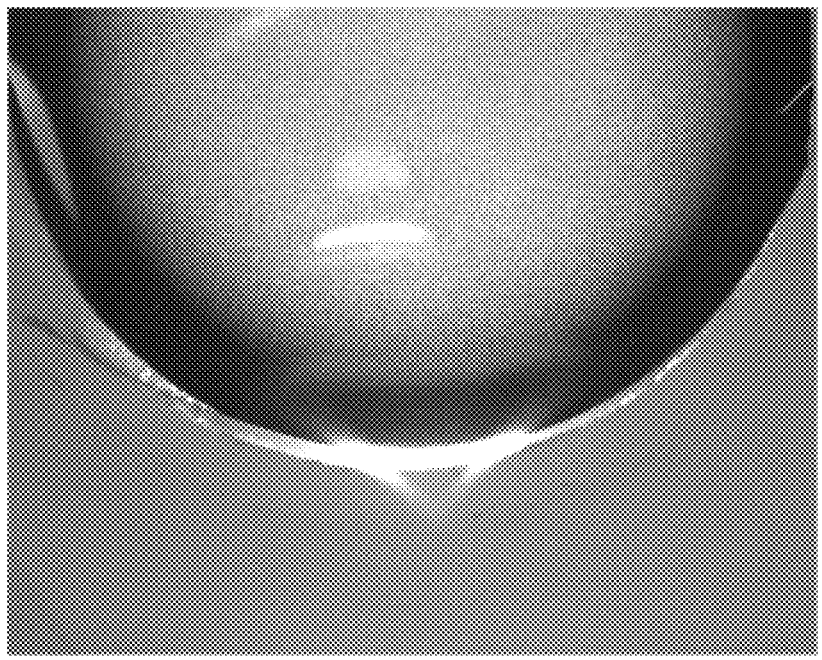
FIG. 16: Avansee lens, 20× and 100× magnification.
Figure 16:
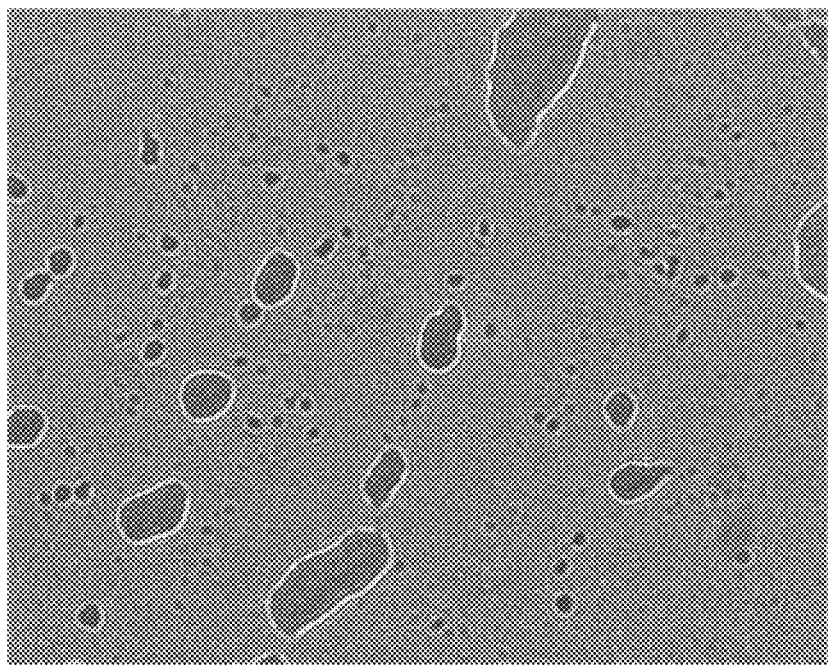
Figure 17:
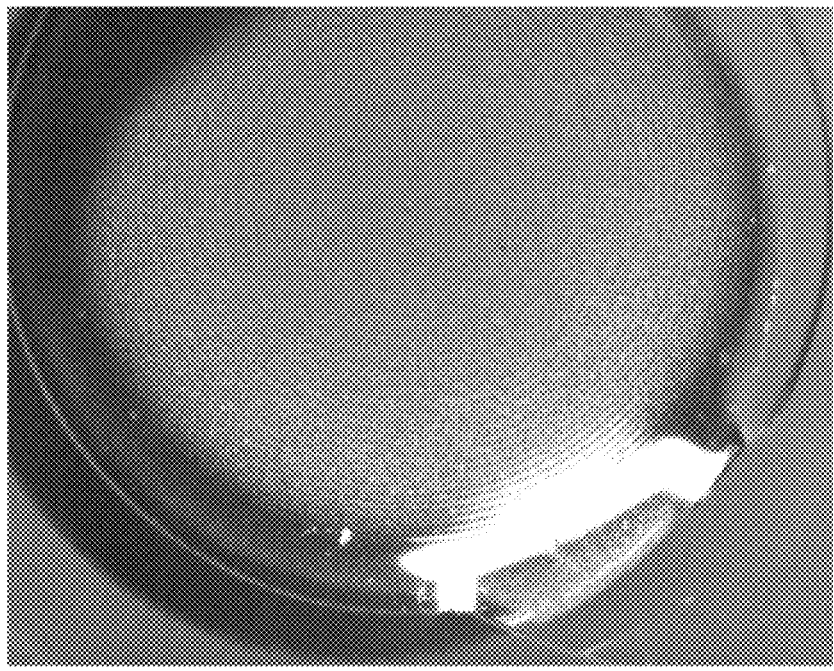
FIG. 17: Tecnis lens, 20× and 100× magnification.
Figure 17:
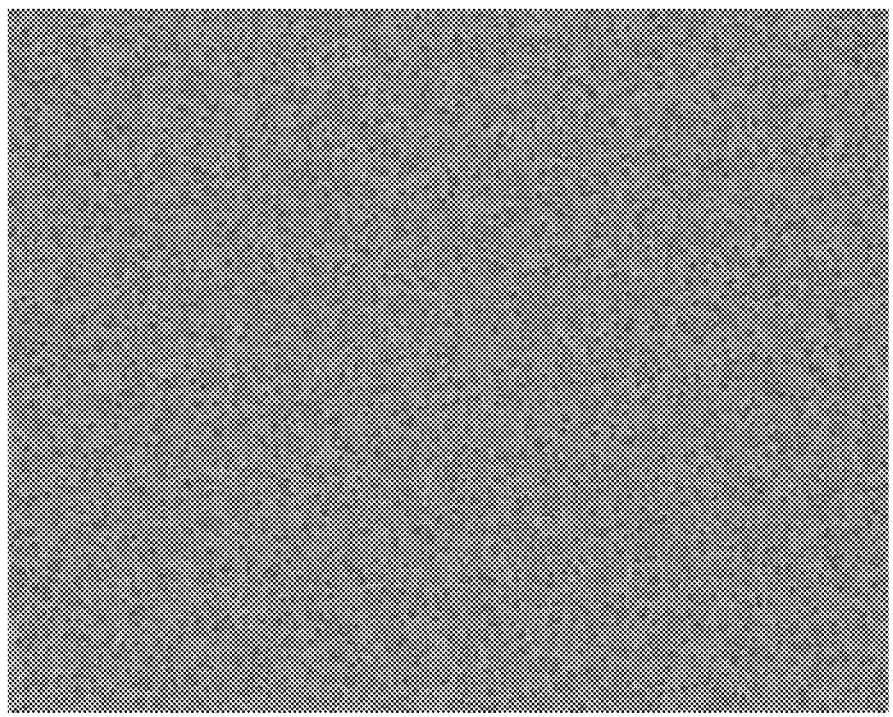
Figure 18:
FIG. 18: Asquelio lens, 20× and 100× magnification.
Figure 18:
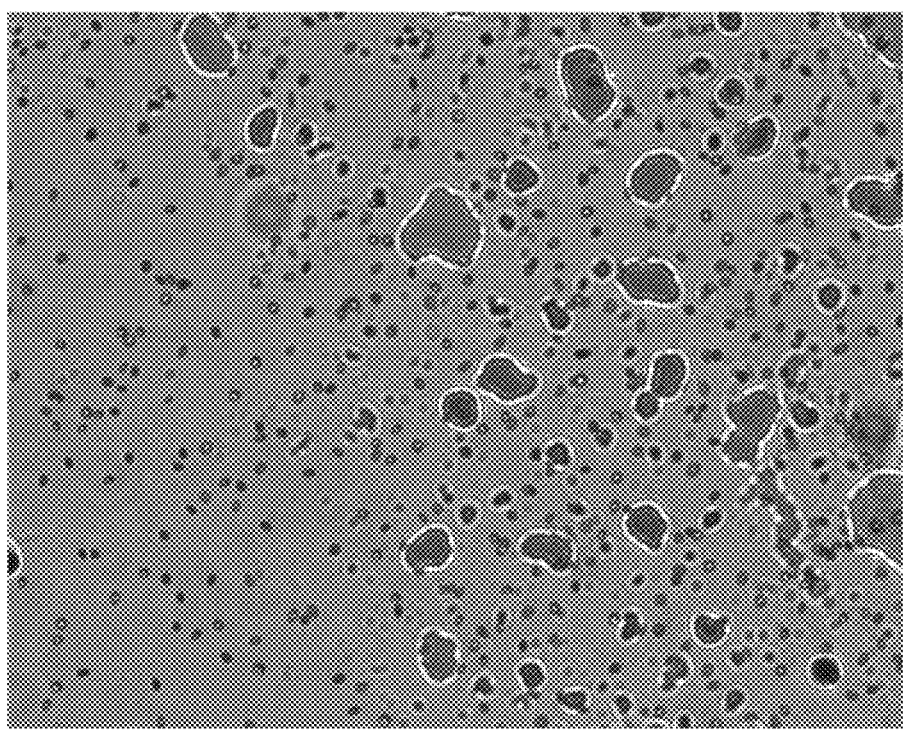
Figure 19:
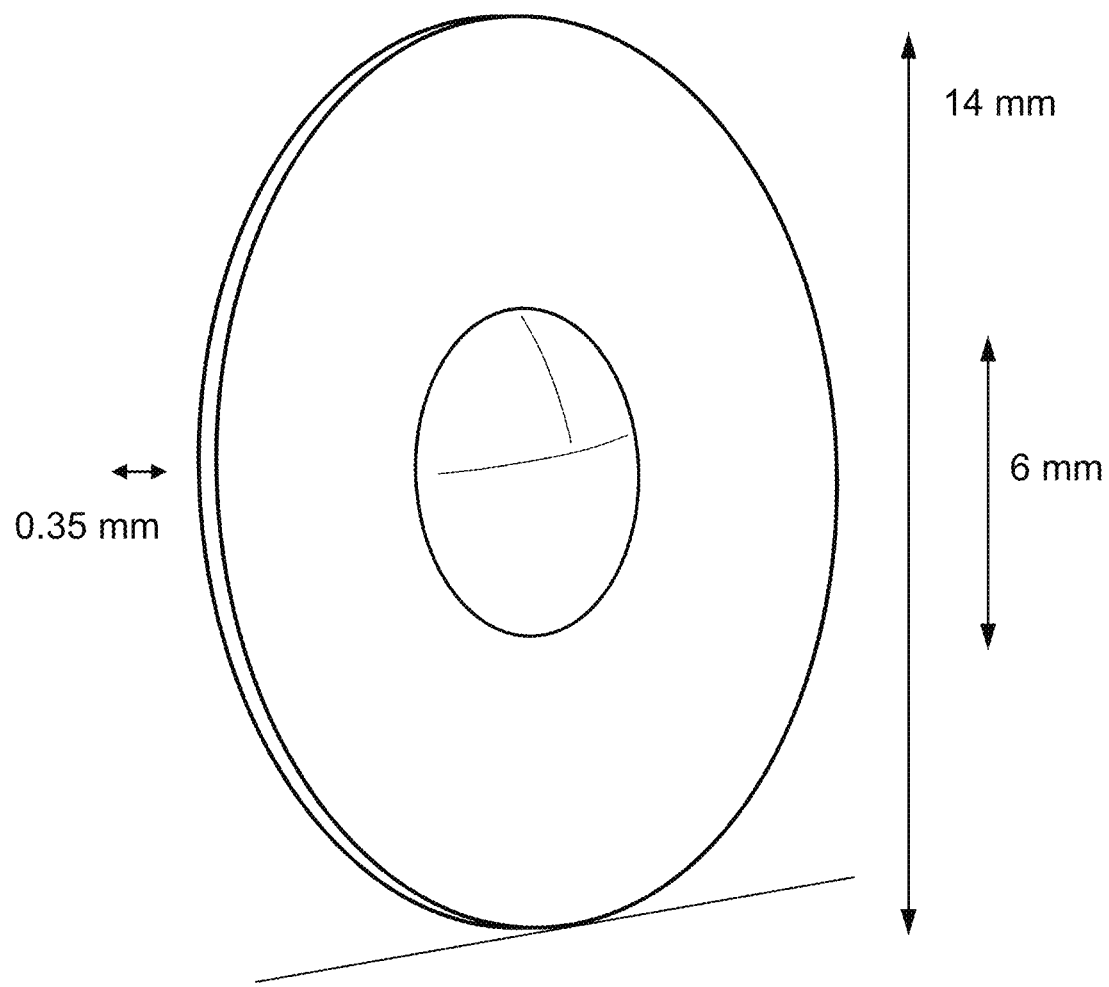
FIG. 19: Model of a so called "flying saucer".

The intraocular lens compositions defined herein have a tackiness within the limits necessary for application in intraocular surgical procedures. The tackiness can be evaluated by folding a specimen shaped like a flying saucer of about 14 mm in diameter with an optical part of about 6 mm and a plan parallel flap circumference with a thickness of about 0.35 mm (see FIG. 9) in two and applying pressure with the fingers for one or two seconds or more, so that one half of the flap of the specimen touches the other half of the same specimen, and is compressed against it. Subsequently, the pressure is released. A non-tacky specimen will readily start to recover its original shape, while a sticky specimen will remain folded, as the interactions between the two halves of the lens are too strong to let the lens unfold. Additionally, and most importantly, when finished lenses of the present formulation were tested for injection using an injector with a nozzle of 2.2 mm and a viscoelastic medium, unfolding due to tackiness was never observed.

The intraocular lens compositions defined herein are soft enough to be foldable. They have an unfolding time of 1-150 seconds, preferably 3-120 seconds, more preferably 5 to 30 seconds. The unfolding time can be determined by recording a video of the lens after it has passed through an injector nozzle and deposited in a small water bath at 26° C. (simulating surgery conditions), so that the unfolding process can be precisely observed and timed.

The present invention thus also provides an intraocular lens, a keratoprosthesis, a corneal ring, a corneal implant, or a corneal inlay, comprising an intraocular lens composition as defined above.

Methods for Making the Intraocular Lens Composition

The present intraocular lens composition can be made by generically known polymerization process, using the above-defined mixture of monomers as starting mixture for the polymerization. In preferred embodiments, the polymerization process is a radical polymerization process. In further preferred embodiments, the polymerization is performed in a single step, using the mixture of monomers as reactants. The mixture of monomers may suitably comprise a solvent, as is known in the art. Preferably however, the polymerization mixture consists of only the monomers to be polymerized, as well as a polymerization initiator.

Thus, the invention also pertains to a method of preparing an intraocular lens composition as defined above, comprising
1) preparing a mixture of the monomers defined above;
2) preferably, adding a radical polymerization initiator
3) allowing the polymerization to occur;
4) Performing an extraction with a suitable solvent to eliminate residual unreacted monomers or other impurities, if necessary.

Suitable polymerization initiators are radical polymerization initiators. Such compounds are well-known, and any compound known for this purpose can be used. Preferably, the initiator is a diazo initiator, such as for example 2,2-azobis(2,4-dimethylvaleronitrile), 2,2'-azobis(2-methylpropionitrile), azobisisobutyronitrile lauroyl peroxide, benzoylperoxide, but also photoinitiators can be used, such as for example phenylbis(2,4,6-trimethylbenzoyl)phosphine oxide. Further preferably, the initiator is an organic peroxide, such as for example di-t-butyl peroxide, benzoyl peroxide, lauroyl peroxide or methyl ethyl ketone peroxide.

The quantity of initiator depends on the type of initiator and the specific monomer mixture, as is known to the skilled person. Generally, the quantity of initiator can be 0.1-2 wt. %, expressed as wt. % of the monomer mixture, preferably 0.2-1.5 wt. %, more preferably 0.5-1 wt. %.

In certain embodiments, the atmospheric content of oxygen needs to be reduced before the polymerization, but in other embodiments of the present composition, the polymerization can be performed in an atmosphere comprising oxygen, such as air. This is an advantage, as it prevents the use of an inert atmosphere, as is conventional. The polymerization of the present composition can for instance be performed in a gas atmosphere where oxygen is about 21%. Preferably the polymerization is performed in an atmosphere with an oxygen content of preferably less than 5%, and most preferably less than 1%.

Alternatively, the polymerization can be performed in an inert atmosphere, as is known in the art. An inert atmosphere may comprise nitrogen or argon (or a mixture thereof), or other known inert gas(es).

Polymerization is generally performed in a mold formed of polypropylene or other suitable material, which provides the shape and the optic of the lens to be obtained or made in sheet or button form of sufficient thickness to shape the lens out by classical lathe cut technology as known in the state of the art.

Suitably, after the polymerization is complete, the obtained polymeric composition is removed from the mold, and may optionally be cut so as to form the haptic portion of the lens. When completed, the lens is suitably stored dry or hydrated in a water based system.

For the purpose of clarity and a concise description features are described herein as part of the same or separate embodiments. However, it will be appreciated that the scope of the invention may include embodiments having combinations of all or some of the features described. The invention will now be illustrated by the following, non-limiting examples.

EXAMPLES ACCORDING TO THE INVENTION

Examples 1 to 13 show the components of compositions in accordance with the present invention.

Example 1

| component | weight % |
| --- | --- |
| Phenyl methacrylate | 21.8 |
| Cyclohexyl acrylate | 28.8 |
| Di(ethylene glycol) ethyl ether acrylate | 38.1 |
| Poly(ethylene glycol 700) diacrylate | 7.0 |
| Trimethylolpropane triacrylate | 4.4 |

Example 2

| component | weight % |
| --- | --- |
| Butyl methacrylate | 68.4 |
| Di(ethylene glycol)ethylether acrylate | 19.9 |
| Poly(ethylene glycol 700) diacrylate | 7.8 |
| Tri(propylene glycol) diacrylate | 3.9 |

Example 3

| component | weight % |
| --- | --- |
| Benzyl acrylate | 15.5 |
| Isobornyl methacrylate | 29.5 |
| Di(ethylene glycol) ethyl ether acrylate | 44.7 |
| Poly(ethylene glycol 1000) dimethacrylate | 6.2 |
| Ethylene glycol dimethacrylate | 4.1 |

Example 4

| component | weight % |
| --- | --- |
| Ethyl methacrylate | 30.0 |
| 2-Methoxyethyl acrylate | 51.8 |
| 2-Methoxyethyl methacrylate | 8.5 |
| Poly(ethylene glycol 400) diacrylate | 4.8 |
| Ethylene glycol dimethacrylate | 4.8 |

Example 5

| component | weight % |
| --- | --- |
| Benzyl methacrylate | 30.6 |
| Cyclohexyl acrylate | 14.9 |
| Di(ethylene glycol) methyl ether methacrylate | 48.0 |
| Poly(ethylene glycol 1000) dimethacrylate | 4.4 |
| Trimethylolpropane trimethacrylate | 2.1 |

Example 6

| component | weight % |
| --- | --- |
| Propyl methacrylate | 21.7 |
| 2-(2-Methoxyethoxy)ethyl methacrylate | 70.2 |
| Poly(propylene glycol 800) diacrylate | 5.4 |
| Trimethylolpropane trimethacrylate | 2.7 |

Example 7

| component | weight % |
| --- | --- |
| 2-Phenylethyl acrylate | 10.0 |
| Cyclohexyl methacrylate | 33.1 |
| 2-Methoxyethyl acrylate | 45.4 |
| Poly(ethylene glycol 400) diacrylate | 8.0 |
| Ethylene glycol dimethacrylate | 3.5 |

Example 8

| component | weight % |
| --- | --- |
| tert-Butyl acrylate | 52.4 |
| Tetrahydrofurfuryl acrylate | 35.1 |
| Poly(ethylene glycol 700) diacrylate | 9.4 |
| Tri(ethylene glycol) dimethacrylate | 3.1 |

Example 9

| component | weight % |
| --- | --- |
| Benzyl acrylate | 16.7 |
| 1-Adamantyl methacrylate | 25.0 |
| Triethylene glycol methyl ether methacrylate | 36.7 |
| 2-Ethoxyethyl methacrylate | 16.7 |
| Poly(ethylene glycol 600) diacrylate | 2.5 |
| Trimethylolpropane triacrylate | 2.5 |

Example 10

| component | weight % |
| --- | --- |
| Ethyl methacrylate | 22.2 |
| 2-Methoxyethyl acrylate | 23.0 |
| 2-Ethoxyethyl methacrylate | 44.0 |
| Poly(ethylene glycol 550) dimethacrylate | 8.6 |
| Tetra (ethylene glycol) dimethacrylate | 2.2 |

Example 11

| component | weight % |
| --- | --- |
| 2-Phenylethyl methacrylate | 26.9 |
| Isobornyl methacrylate | 14.4 |
| 2-Methoxyethyl acrylate | 48.3 |
| Poly(ethylene glycol 400) diacrylate | 6.7 |
| Ethylene glycol dimethacrylate | 3.6 |

Example 12

| component | weight % |
| --- | --- |
| Methyl methacrylate | 26.5 |
| 2-(2-Methoxyethoxy)ethyl methacrylate | 65.3 |
| Poly(propylene glycol 800) diacrylate | 4.1 |
| Tetra (ethylene glycol) diacrylate | 4.1 |

Example 13

| component | weight % |
| --- | --- |
| 2-Phenylethyl acrylate | 8.3 |
| 1-Adamantyl methacrylate | 30.3 |
| 2-Methoxyethyl acrylate | 15.9 |
| Di(ethylene glycol) ethyl ether acrylate | 34.6 |
| Poly(ethylene glycol 550) dimethacrylate | 8.2 |
| Di (ethylene glycol) dimethacrylate | 2.7 |

The components were mixed together and stirred at room temperature until homogeneity is reached. The mixture was then filtered through a 0.45 μm inert filter, and used to fill the molds, which were made by polypropylene or other suitable material.

Next, the filled molds were placed in an oven, and the polymer mixture was cured by increasing the temperature from room temperature (about 20° C.) to 90° C. in 5 hours, followed by keeping the temperature at 90° C. for further 6 hours. As understood by the person skilled in the art, this thermal profile can be modified according to the specific mixture, in order to tune the results.

At this point, the molds were allowed to cool down to room temperature, then they were opened, and the pieces were recovered. Depending on the type of mold, further machining may be performed, for example lathing and milling, as is known in the art. Extraction of the residual unreacted monomers may be considered.

COMPARATIVE EXAMPLES

Examples 14-17 show composition outside of the scope of the present invention, which do present formation of vacuoles or other problems.

Example 14

| component | weight % |
| --- | --- |
| Benzyl acrylate | 16.5 |
| Isobornyl methacrylate | 31.4 |
| Di(ethylene glycol) ethyl ether acrylate | 47.6 |
| Ethylene glycol dimethacrylate | 4.4 |

Example 15

| component | weight % |
| --- | --- |
| Benzyl methacrylate | 32.0 |
| Cyclohexyl acrylate | 15.6 |
| Di(ethylene glycol) methyl ether methacrylate | 50.2 |
| Trimethylol propane trimethacrylate | 2.1 |

Example 16

| component | weight % |
| --- | --- |
| Butyl methacrylate | 74.2 |
| Di(ethylene glycol)ethylether acrylate | 21.6 |
| Tri(propylene glycole) diacrylate | 4.2 |

Example 17

| component | weight % |
| --- | --- |
| Ethyl methacrylate | 21.0 |
| 2-Methoxyethyl acrylate | 26.3 |
| 2-Ethoxyethyl methacrylate | 50.3 |
| Tetra (ethylene glycol) dimethacrylate | 2.5 |

Example 18

| component | weight % |
| --- | --- |
| Benzyl acrylate | 17.1 |
| 1-Adamantyl methacrylate | 25.6 |
| Triethylene glycol methyl ether methacrylate | 37.7 |
| 2-Ethoxyethyl methacrylate | 17.1 |
| Poly(ethylene glycol 600) diacrylate | 2.6 |

The lenses were prepared from these compositions according to the same procedure described above for examples 1-13.

The present invention improves on the known lens materials, and provides a intraocular lens composition which presents no vacuoles at all even under harsh testing conditions, has a properly tuned hardness to provide comfortable unfolding speed, ease to fold and comfortable injection force, and does not present prohibitive tackiness. Additionally, the refractive index (RI) is in all cases within accepted values, and the optical quality (MTF) is consistently very good.

Glistenings Tests

The glistenings test is performed by placing a lens in a 7 ml vial filled with a 0.9% NaCl aqueous solution, keeping the vial at 50° C. for 16 h or longer, cooling at room temperature (ca. 20° C.) for 0.5-1 h, taking the lens out of the vial, and analyzing it under a microscope (Olympus BX50) in darkfield illumination with a magnification from 20× to 100×, and when needed up to 500×. On the microscope, retroillumination was used, and no filters were added. The formation of vacuoles is assessed visually.

The results are shown in FIGS. 1-13 for lenses of examples 1-13. It can be seen that no vacuoles were observed in these lenses prepared in accordance with the invention. The results of the glistenings tests are summarized in table 1, together with other parameters.

Lenses of examples 14-18 are outside the scope of the invention. Lenses of examples 14-17 do present vacuoles; lenses of example 18 turn white after hydrating in water, and also present a few vacuoles already before performing the glistening test. These results are summarized in table 2.

For comparison, the glistening test was performed with the following commercially available lenses:
AcrySof® (Alcon)
iSert® 255 (HOYA Surgical Optics)
Avansee™ (Kowa pharmaceutical Europe)
Tecnis® (Johnson & Johnson Surgical Vision)
Asgelio™ (AST Products)

The results are shown in FIGS. 14-18 and summarized in table 3.

With Alcon AcrySof (FIG. 14), Hoya 255 (FIG. 15) and Tecnis (FIG. 17) lenses, many vacuoles are visible. The hazy appearance of the Avansee lens (FIG. 16) after the glistening test can be attributed to the formation of a myriad of very small vacuoles. In the 100× picture, residual droplets of water are visible, which were not forcefully removed in order not to affect the glistenings inside the material.

With the Asqelio lens (FIG. 18) vacuoles are also visible. In the 100× picture, residual droplets of water are visible, which were not forcefully removed in order not to affect the glistenings inside the material.

TABLE 1

Results of glistening tests on examples 1-13.

| example no. | glistenings | unfolding speed | tackiness | RI | MTF |
| --- | --- | --- | --- | --- | --- |
| 1 | No vacuoles | 50 s | none | 1.5011 | 0.54 |
| 2 | No vacuoles | 5 s | very low | 1.4800 | 0.54 |

TABLE 1-continued

Results of glistening tests on examples 1-13.

| example no. | glistenings | unfolding speed | tackiness | RI | MTF |
|---|---|---|---|---|---|
| 3 | No vacuoles | 60 s | none | 1.5023 | 0.52 |
| 4 | No vacuoles | 5 s | none | 1.4811 | 0.54 |
| 5 | No vacuoles | 50 s | low | 1.5145 | 0.55 |
| 6 | No vacuoles | 10 s | very low | 1.4844 | 0.54 |
| 7 | No vacuoles | 60 s | none | 1.4986 | 0.54 |
| 8 | No vacuoles | 10 s | low | 1.4785 | 0.55 |
| 9 | No vacuoles | 75 s | none | 1.5064 | 0.51 |
| 10 | No vacuoles | 10 s | very low | 1.4837 | 0.55 |
| 11 | No vacuoles | 105 s | none | 1.5065 | 0.54 |
| 12 | No vacuoles | 10 s | very low | 1.4842 | 0.54 |
| 13 | No vacuoles | 90 s | none | 1.5024 | 0.48 |

Unfolding speed: measured after injection in a water bath at 26° C. (an injector tip with a diameter of 2.2 mm was used; all lenses were injected with the aid of an ophthalmic viscoelastic solution). Tackiness: based on observation while folding a specimen shaped like a flying saucer in two; however, none of the lenses in the test failed to unfold after injection, therefore the tackiness can be considered to be very low in all cases. RI: measured with a refractometer by Index Instrument Limited, model CRL 12-70, using a wavelength of 589 nm at room temperature (all the samples were hydrated in demineralized water, except example 13, which was hydrated in a 0.9% NaCl aq. solution). The MTF was measured on a PMTF by Lamda-X (all the samples were hydrated in demineralized water, except example 13, which was hydrated in a 0.9% NaCl aq. solution).

TABLE 2

Results of glistening tests on comparative examples 14-18.

| example no. | glistenings |
|---|---|
| 14 | a few vacuoles |
| 15 | many vacuoles |
| 16 | many vacuoles |
| 17 | a few vacuoles and very hazy |
| 18 | (it turns white when hydrated) |

TABLE 3

Results of glistening tests on selected commercially available lenses.

| Test lens | glistenings |
|---|---|
| AcrySof ® (Alcon) | Many vacuoles |
| iSert ® 255 (HOYA) | Many vacuoles |
| Avansee ™ (Kowa) | Very hazy, probably due to a myriad of very small vacuoles |
| Tecnis ® (Johnson & Johnson Surgical Vision) | Many vacuoles |
| Asqelio ™ (AST Products) | Many vacuoles |

ADDITIONAL COMPARATIVE EXAMPLES

Example 19

| component | parts by weight | weight % |
|---|---|---|
| 2-Phenoxyethyl acrylate | 40 | 31.0 |
| 2-Hydroxyethyl methacrylate | 25 | 19.4 |
| Ethyl acrylate | 60 | 46.5 |
| Ethylene glycol dimethacrylate | 4 | 3.1 |

Example 20

| component | parts by weight | weight % |
|---|---|---|
| 2-Phenoxyethyl acrylate | 60 | 50.4 |
| 2-Hydroxyethyl methacrylate | 15 | 12.6 |
| Ethyl acrylate | 40 | 33.6 |
| Ethylene glycol dimethacrylate | 4 | 3.4 |

Examples 19 and 20 represent a comparison with products from U.S. Pat. No. 6,140,438. Examples 4 and 6 from U.S. Pat. No. 6,140,438 were reproduced as indicated in the said document. The polymerizable components identified in tables 19 and 20 and 1 part by weight per 100 parts by weight of the total amount of polymerizable components, of 2,2'-azobis(2,4-dimethylvaleronitrile), as polymerization initiator, were mixed, and the mixture was poured into a casting mold having a desired intraocular lens shape. This casting mold was put into an oven and heat polymerization molding was carried out at 50° C. for 24 hrs. Then, the casting mold was transferred to an air circulating dryer and heated from 65 to 130° C. at a rate of 10° C./hr and then cooled to room temperature. Then, LED black light irradiation was carried out over one hour by means of an irradiation apparatus. Thereafter, the obtained polymer was taken out from the casting mold and further dried for 2 days at 50° C. in an oven.

Identically prepared lens compositions were subjected to the curing program described for examples 1-13, instead of to the curing program described in U.S. Pat. No. 6,140,438. The result was the same for both curing programs.

Figure 20:
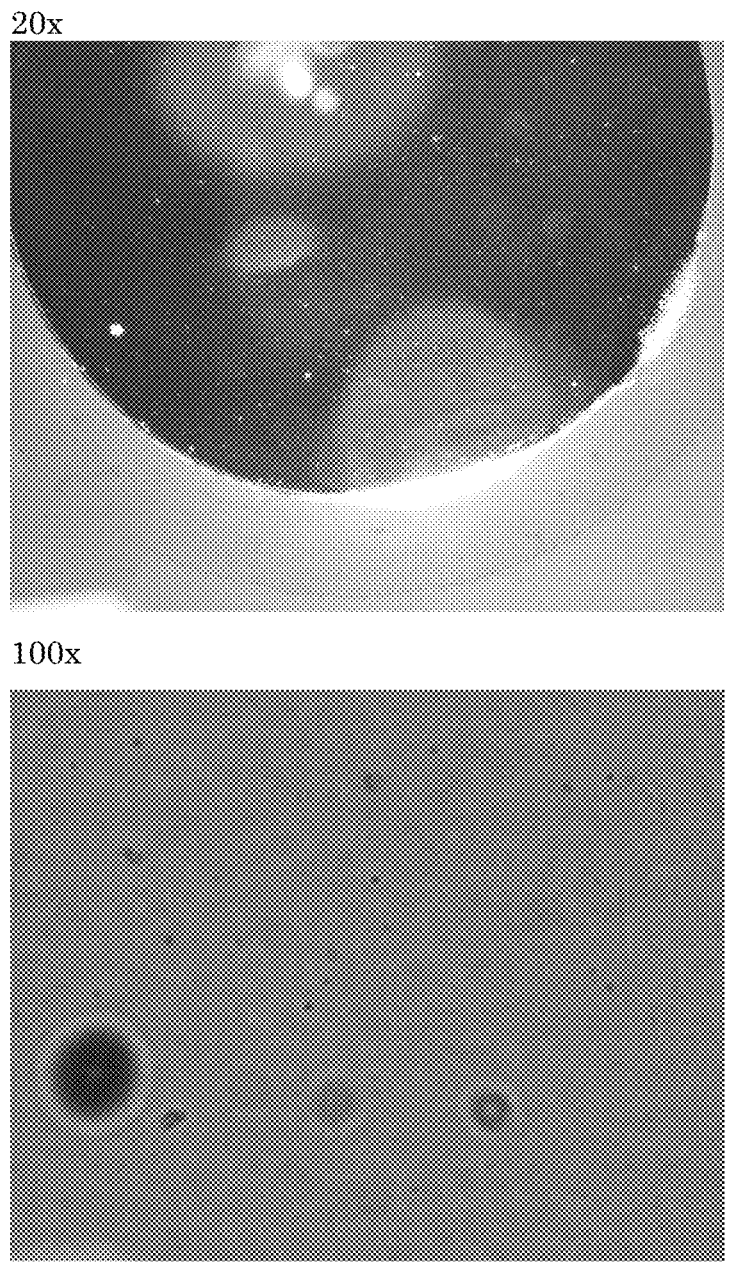
FIG. 20: Lens from example 19, 20× and 100× magnification.
Figure 21:
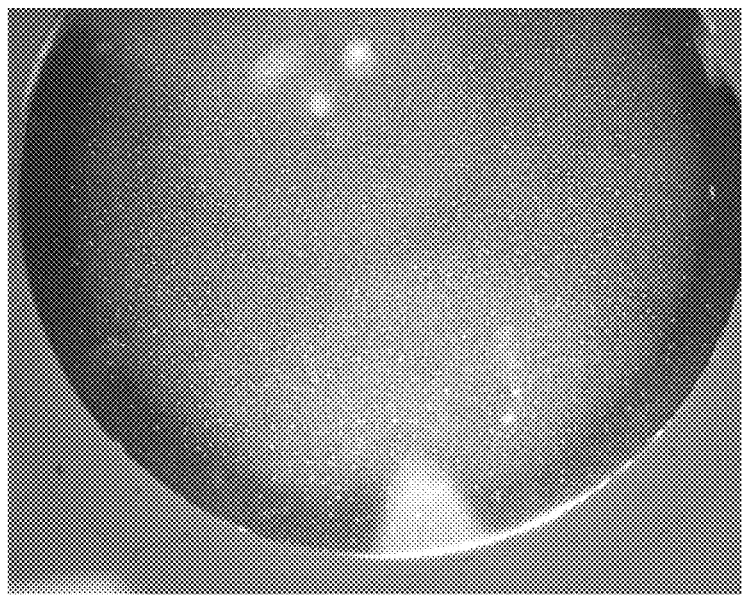
FIG. 21: Lens from example 20, 20× and 100× magnification.
Figure 21:
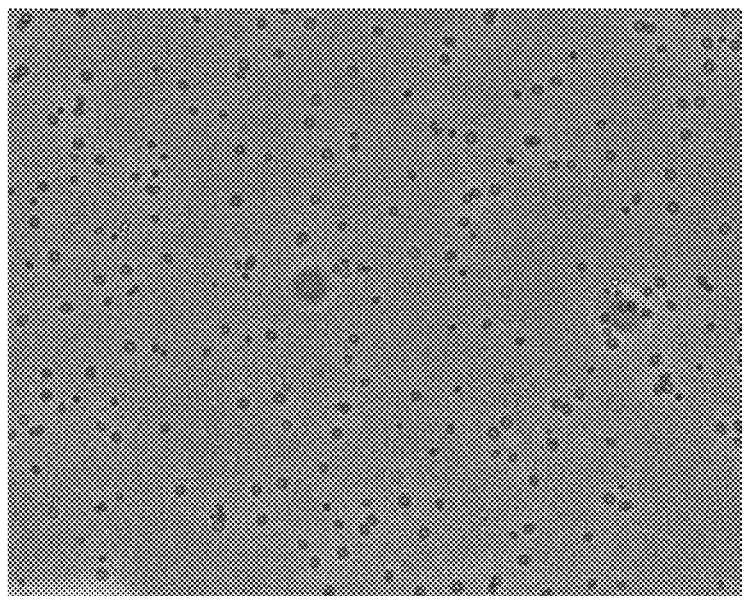

Glistenings tests were performed using the harsh method described for examples 1-13. The results are shown in FIGS. 20-21 for lenses of examples 19 and 20 respectively and summarized in table 4.

TABLE 4

Results of glistening tests on comparative examples 19-20.

| example no. | glistenings |
|---|---|
| 19 | a few vacuoles and hazy |
| 20 | many vacuoles and very hazy |

As can be seen in table 4, the lens materials prepared from the intraocular lens composition according to U.S. Pat. No. 6,140,438 contain vacuoles and are hazy when observed under LED light. Thus, even if under the soft conditions and short time frame applied in U.S. Pat. No. 6,140,438 the lenses in U.S. Pat. No. 6,140,438 are said to contain no vacuoles, harsher conditions mimicking an accelerated aging process under in vivo conditions show that the lenses in U.S. Pat. No. 6,140,438 in fact are not vacuole-free, and do develop haze. It follows that the lens materials according to U.S. Pat. No. 6,140,438 perform significantly worse compared to lens materials according to the invention, which exhibit no vacuoles and no hazing.

The invention claimed is:
1. An intraocular lens composition comprising a polymeric mixture of the monomers:
a short crosslinker, comprising two or more (meth)acrylate portions and a connecting portion located between the two (meth)acrylate portions and which connecting portion is connected to the (meth)acrylate portions through ester groups, wherein the longest linear atomic sequence between the oxygen atom of the ester group connecting the first (meth)acrylate portion to the connecting portion and the oxygen atom of the ester group connecting the second (meth)acrylate portion to the connecting portion is 1-11 atoms;
a long crosslinker, comprising two or more (meth)acrylate portions and a connecting portion located between the two (meth)acrylate portions and which connecting portion is connected to the (meth)acrylate portions through ester groups, wherein the longest linear atomic sequence between the oxygen atom of the ester group connecting the first (meth)acrylate portion to the connecting portion and the oxygen atom of the ester group connecting the second (meth)acrylate portion to the connecting portion is 12 atoms or more:
one or more (meth)acrylate monomers of formula (I)

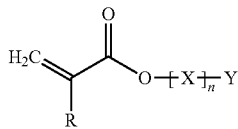

(I)

wherein:
X is —(C1-C4 alkyl)-O—, —(C1-C4 alkyl)-S—, —(C1-C4 alkyl)-N— or a C1-C8 alkyl group, which C1-C8 alkyl group comprises a cycloalkyl and wherein one of the C-atoms is replaced by a heteroatom selected from the group consisting of O, S and N;
Y is absent or —C1-C4 alkyl;
n is 1-6;
R is H or CH3;
one or more C1-C4-alkyl(meth)acrylate monomers of formula (II)

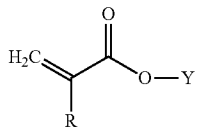

(II)

wherein:
Y is —C1-C4 alkyl;
R is H or CH3;
or a combination of at least one phenyl-C1-C4-alkyl (meth)acrylate of formula (III)

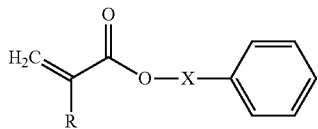

(III)

wherein:
X is absent or —C1-C4 alkyl;
R is H or CH3;
and at least one cycloalkyl(meth)acrylate of formula (IV)

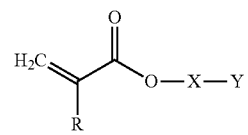

(IV)

wherein:
X is absent, a C1-C5 alkyl group, or a —[(C1-C4 alkyl)-O]$_n$— group wherein n is 1-8;
Y is a C3-C18 alkyl group comprising at least one cycloalkyl portion, which C3-C18 alkyl group optionally comprises one or more heteroatoms selected from the group consisting of O and N;
R is H or CH3
wherein the longest linear atomic sequence defined for the long and short crosslinker comprises C, optionally O, and optionally N, wherein the total of C atoms exceeds the total of O and N atoms, and wherein said linear atomic sequence comprises side groups selected from the group consisting of $R^2$, $OR^2$, $SR^2$, $NR^2_2$, $COOR^2$ or F, wherein $R^2$ is H, alkyl, cycloalkyl, heterocycloalkyl, an aromatic portion, or any combination thereof, which $R^2$ has a molecular weight of at most 100 Da,
comprising a polymeric mixture of (a)
5-40 wt. %, phenyl methacrylate
10-55 wt. % cyclohexyl acrylate
15-55 wt. % di(ethylene glycol) ethyl ether acrylate
1-20 wt. % poly(ethylene glycol) diacrylate with a molecular weight of 250-5000 Da
2-10 wt. % trimethylolpropane triacrylate
or (b)
5-80 wt. % butyl methacrylate
3-45 wt. % di(ethylene glycol) ethyl ether acrylate
1-15 wt. % poly(ethylene glycol) diacrylate with a molecular weight of 250-1800 Da
0.1-8 wt. % tri(propylene glycole) diacrylate
or (c)
5-65 wt. % benzyl acrylate
5-75 wt. % isobornyl methacrylate
15-80 wt. % di(ethylene glycol) ethyl ether acrylate
1-15 wt. % poly(ethylene glycol) dimethacrylate with a molecular weight of 250-5000 Da
0.1-8 wt. % ethylene glycol dimethacrylate
or (d)
1-60 wt. % ethyl methacrylate
3-75 wt. % methoxyethyl acrylate or 2-85 wt. % methoxyethylmethacrylate and combinations thereof
1-15 wt. % poly(ethylene glycol) diacrylate with a molecular weight of 200-5000 Da
0.1-8 wt. % ethylene glycol dimethacrylate
or (e)
5-75 wt. % benzyl methacrylate
25-75 wt. % cyclohexyl acrylate
15-80 wt. % di(ethylene glycol) methyl ether methacrylate
1-15 wt. % poly(ethylene glycol) dimethacrylate with a molecular weight of 250-5000 Da
0.1-8 wt. % trimethylol propane trimethacrylate or (f)
1-65 wt. % propyl methacrylate
5-85 wt. % 2-(2-methoxyethoxy) ethyl methacrylate
1-15 wt. % poly(propylene glycol) diacrylate with a molecular weight of 230-2000 Da
0.1-8 wt. % trimethylolpropane trimethacrylate
or (g)
1-55 wt. % 2-phenylethyl acrylate
3-65 wt. % cyclohexyl methacrylate
15-90 wt. % 2-methoxyethyl acrylate
1-15 wt. % poly(ethylene glycol) diacrylate with a molecular weight of 200-5000 Da
0.1-8 wt. % ethylene glycol dimethacrylate
or (h)
1-70 wt. % tert-butyl acrylate
3-75 wt. % tetrahydrofurfuryl acrylate
1-15 wt. % poly(ethylene glycol) diacrylate with a molecular weight of 200-2000 Da
0.1-8 wt. % tri(ethylene glycol) dimethacrylate
or (i)
1-55 wt. % benzyl acrylate
2-45 wt. % 1-adamantyl methacrylate549
15-80 wt. % triethylene glycol methyl ether methacrylate or 2-45 wt. % 2-ethoxyethyl methacrylate and combinations thereof
1-15 wt. % poly(ethylene glycol) diacrylate with a molecular weight of 200-5000 Da
0.1-8 wt. % trimethylolpropane triacrylate
or (j)
1-75 wt. % ethyl methacrylate
2-75 wt. % 2-methoxyethyl acrylate or 2-75 wt. % 2-ethoxyethyl methacrylate and combinations thereof
1-15 wt. % poly(ethylene glycol) dimethacrylate with a molecular weight of 200-2000 Da
0.1-8 wt. % tetra (ethylene glycol) dimethacrylate
or (k)
1-55 wt. % 2-phenylethyl methacrylate
2-55 wt. % isobornyl methacrylate
15-80 wt. % 2-methoxyethyl acrylate
1-15 wt. % poly(ethylene glycol) diacrylate with a molecular weight of 200-5000 Da
0.1-8 wt. % ethylene glycol dimethacrylate
or (l)
1-65 wt. % methyl methacrylate
10-85 wt. % 2-(2-methoxyethoxy) ethyl methacrylate
1-15 wt. % poly(propylene glycol) diacrylate with a molecular weight of 230-2000 Da
0.1-8 wt. % tetra (ethylene glycol) diacrylate
or (m)
1-55 wt. % 2-phenylethyl acrylate
2-45 wt. % 1-adamantyl methacrylate
5-80 wt. % 2-methoxyethyl acrylate or 2-75 wt. % di(ethylene glycol) ethyl ether acrylate and combinations thereof
1-15 wt. % poly(ethylene glycol) dimethacrylate with a molecular weight of 200-5000 Da
0.1-8 wt. % di(ethylene glycol) dimethacrylate.

2. An intraocular lens composition according to claim 1, further comprising in said mixture a UV light-filtering chromophore in a quantity suitable to absorb at least 50% of optical radiation with a wavelength between 350 and 400 nm, or a blue light-filtering chromophore in a quantity suitable to absorb at least 50% of optical radiation with a wavelength between 400-500 nm and combinations thereof.

3. An intraocular lens composition according to claim 1 having a water uptake, measured by weight, of less than 10 wt. %.

4. An intraocular lens composition according to claim 1 for use as a foldable implantable ophthalmic device in the treatment of cataract and refractive surgery.

5. An intraocular lens, a keratoprosthesis, a corneal ring, a corneal implant, or a corneal inlay, comprising an intraocular lens composition as defined in claim 1.

6. A method of preparing an intraocular lens composition according to claim 1, comprising
   1) preparing a mixture of the monomers defined in claim 1;
   2) allowing polymerization of the mixture of monomers.

7. A method according to claim 6, wherein the polymerization is performed in an atmosphere comprising oxygen.

8. A method according to claim 6, wherein the polymerization is performed in an inert atmosphere.

9. A method according to claim 6, wherein the radical polymerization initiator is a diazo-initiator, or wherein the radical polymerization initiator is an organic peroxide, or wherein the radical polymerization initiator is a photo-initiator.

10. A method according to claim 6, comprising after step 1 and before step 2 a step of adding a radical polymerization initiator.

11. A method according to claim 10, comprising after step 2 a step of performing an extraction to remove any side products and/or residual unreacted monomer.

12. A method according to claim 7, wherein the atmosphere comprising oxygen is air.

13. A method according to claim 9, wherein the diazo-initiator is 2,2-azobis(2,4-dimethylvaleronitrile) and/or azobisisobutyronitrile, or wherein the organic peroxide is di-t-butyl peroxide, benzoyl peroxide or methyl ethyl ketone peroxide, or wherein the photo-initiator is phenylbis(2,4,6-trimethylbenzoyl)phosphine oxide.

14. An intraocular lens composition according to claim 1, comprising a polymeric mixture of
   (a)
   22±5 wt. % phenyl methacrylate
   29±5 wt. % cyclohexyl acrylate
   38±5 wt. % di(ethylene glycol) ethyl ether acrylate
   7±5 wt. % poly(ethylene glycol) diacrylate with a molecular weight of 250-5000 Da
   4±2 wt. % trimethylolpropane triacrylate
   or (b)
   68±5 wt. % butyl methacrylate
   20±5 wt. % di(ethylene glycol) ethyl ether acrylate
   8±5 wt. % poly(ethylene glycol) diacrylate with a molecular weight of 250-1800 Da
   4±2 wt. % tri(propylene glycole) diacrylate
   or (c)
   16±5 wt. % benzyl acrylate
   30±5 wt. % isobornyl methacrylate
   45±5 wt. % di(ethylene glycol) ethyl ether acrylate
   6±5 wt. % poly(ethylene glycol) dimethacrylate with a molecular weight of 250-5000 Da
   4±2 wt. % ethylene glycol dimethacrylate
   or (d)
   30±5 wt. % ethyl methacrylate
   52±5 wt. % methoxyethyl acrylate and 9±5 wt. % methoxyethylmethacrylate
   5±2 wt. % poly(ethylene glycol) diacrylate with a molecular weight of 200-5000 Da
   5±2 wt. % ethylene glycol dimethacrylate
   or (e)
   31±5 wt. % benzyl methacrylate
   15±5 wt. % cyclohexyl acrylate
   48±5 wt. % di(ethylene glycol) methyl ether methacrylate 4±2 wt. % poly(ethylene glycol) dimethacrylate with a molecular weight of 250-5000 Da
2±1 wt. % trimethylol propane trimethacrylate
or (f)
22±5 wt. % propyl methacrylate
70±5 wt. % 2-(2-methoxyethoxy) ethyl methacrylate
5±2 wt. % poly(propylene glycol) diacrylate with a molecular weight of 230-2000 Da
3±2 wt. % trimethylolpropane trimethacrylate
or (g)
10±5 wt. % 2-phenylethyl acrylate
33±5 wt. % cyclohexyl methacrylate
45±5 wt. % 2-methoxyethyl acrylate
8±5 wt. % poly(ethylene glycol) diacrylate with a molecular weight of 200-5000 Da
4±2 wt. % ethylene glycol dimethacrylate
or (h)
52±5 wt. % tert-butyl acrylate
35±5 wt. % tetrahydrofurfuryl acrylate
9±5 wt. % poly(ethylene glycol) diacrylate with a molecular weight of 200-2000 Da
3±2 wt. % tri(ethylene glycol) dimethacrylate
or (i)
17±5 wt. % benzyl acrylate
25±5 wt. % 1-adamantyl methacrylate
37±5 wt. % triethylene glycol methyl ether methacrylate and 17±5 wt. % 2-ethoxyethyl methacrylate
3±2 wt. % poly(ethylene glycol) diacrylate with a molecular weight of 200-5000 Da
3±2 wt. % trimethylolpropane triacrylate
or (j)
22±5 wt. % ethyl methacrylate
23±5 wt. % 2-methoxyethyl acrylate and 44±5 wt. % 2-ethoxyethyl methacrylate
9±5 wt. % poly(ethylene glycol) dimethacrylate with a molecular weight of 200-2000 Da
2±1 wt. % tetra (ethylene glycol) dimethacrylate
or (k)
27±5 wt. % 2-phenylethyl methacrylate
14±5 wt. % isobornyl methacrylate
48±5 wt. % 2-methoxyethyl acrylate
7±5 wt. % poly(ethylene glycol) diacrylate with a molecular weight of 200-5000 Da
4±2 wt. % ethylene glycol dimethacrylate
or (l)
27±5 wt. % methyl methacrylate
65±5 wt. % 2-(2-methoxyethoxy) ethyl methacrylate
4±2 wt. % poly(propylene glycol) diacrylate with a molecular weight of 230-2000 Da
4±2 wt. % tetra (ethylene glycol) diacrylate
or (m)
8±5 wt. % 2-phenylethyl acrylate
30±5 wt. % 1-adamantyl methacrylate
16±5 wt. % 2-methoxyethyl acrylate and 35±5 wt. % di(ethylene glycol) ethyl ether acrylate
8±5 wt. % poly(ethylene glycol) dimethacrylate with a molecular weight of 200-5000 Da
3±2 wt. % di(ethylene glycol) dimethacrylate.

15. An intraocular lens composition according to claim 2, where in the UV light-filtering chromophore is a benzotriazole-substituted methacrylate.

\* \* \* \* \*